(12) United States Patent
Kandori et al.

(10) Patent No.: US 6,462,540 B1
(45) Date of Patent: Oct. 8, 2002

(54) MAGNETIC FIELD MEASURING APPARATUS WHICH ENABLES EXTERNAL MAGNETIC NOISE CANCELLATION

(75) Inventors: Akihiko Kandori; Tsuyoshi Miyashita, both of Kokubunji; Keiji Tsukada, Kashiwa, all of (JP)

(73) Assignee: Hitachi, Ltd., Tokyo (JP)

( * ) Notice: Subject to any disclaimer, the term of this patent is extended or adjusted under 35 U.S.C. 154(b) by 11 days.

(21) Appl. No.: 09/635,450

(22) Filed: Aug. 10, 2000

(30) Foreign Application Priority Data

Sep. 14, 1999 (JP) ............................... 11-259885

(51) Int. Cl.[7] ................... G01R 33/035; G01R 33/022; A61B 5/05
(52) U.S. Cl. ...................... 324/248; 324/225; 324/261; 505/846; 600/409; 702/191
(58) Field of Search .................... 324/248, 244, 324/260–262, 225; 600/409; 505/162, 846; 702/191, 194, 195

(56) References Cited

U.S. PATENT DOCUMENTS

| 5,187,436 A | * | 2/1993 | Mallick ...................... 324/244 |
| 5,657,756 A | * | 8/1997 | Vrba et al. .............. 324/244 X |
| 5,891,031 A | | 4/1999 | Ohyu ..................... 324/248 X |

FOREIGN PATENT DOCUMENTS

| JP | 9-84777 | 3/1997 |
| JP | 11-47108 | 2/1999 |
| JP | 11-83965 | 3/1999 |

OTHER PUBLICATIONS

J. Vrba et al. "Biomagnetometers for Unshielded and Well Shielded Environments", Clin. Phys. Physiol. Meas., vol. 12, Suppl. B, 1991, pp. 81–86.

H.J.M. ter Brake et al, "Improvement of the Performance of a u–Metal Magnetically Shielded Room by Means of Active Compensation", Meas. Sci. Technol., vol. 2, 1991, pp. 596–601.

* cited by examiner

Primary Examiner—Gerard R. Strecker
(74) Attorney, Agent, or Firm—Mattingly, Stanger & Malur

(57) ABSTRACT

A magnetic field measuring apparatus for precise cancellation of environmental noise includes a plurality of first SQUID gradiometers to detect noise and biomagnetic fields, a plurality of second SQUID gradiometers to detect noise, a driving circuit to drive these gradiometers, and a computer to execute signal processing after collecting the signals detected by these gradiometers. First and second SQUID gradiometers are provided which include first-order gradient pickup coils with the baselines formed by the coils of second gradiometers being shorter than those of first gradiometers. The apparatus cancels noise, from detected biomagnetic signal waveforms, caused by variant noise cancellation rates of the coils of first gradiometers, different baselines of the coils of second gradiometers, and the frequency property of a magnetically shielded room in which the apparatus is installed.

18 Claims, 24 Drawing Sheets

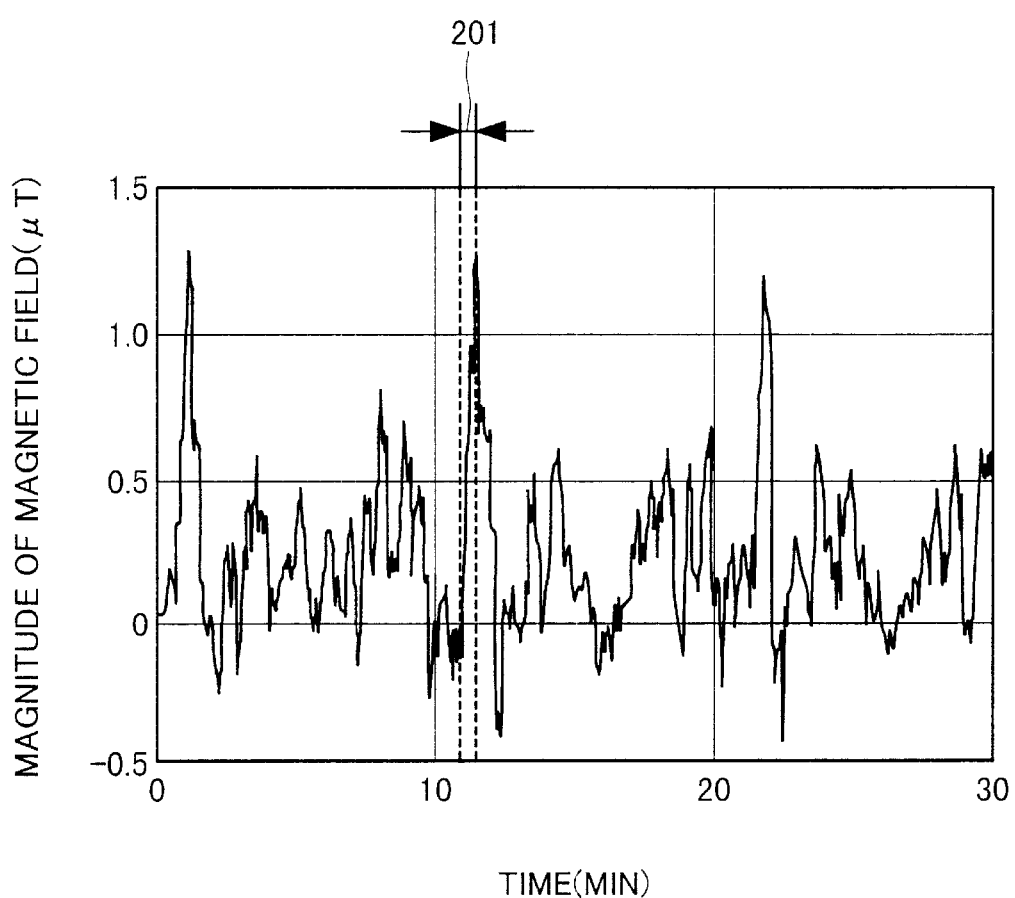

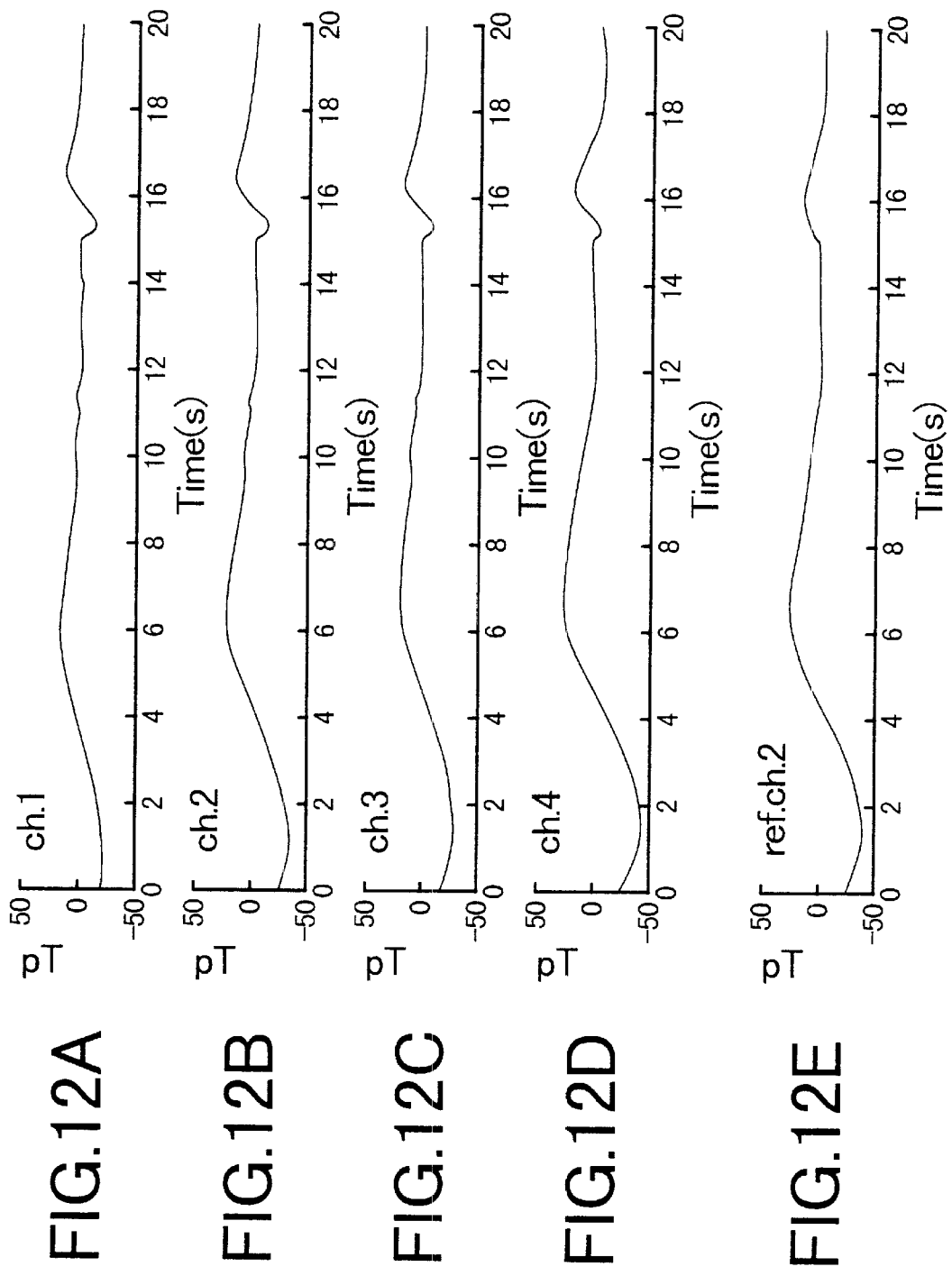

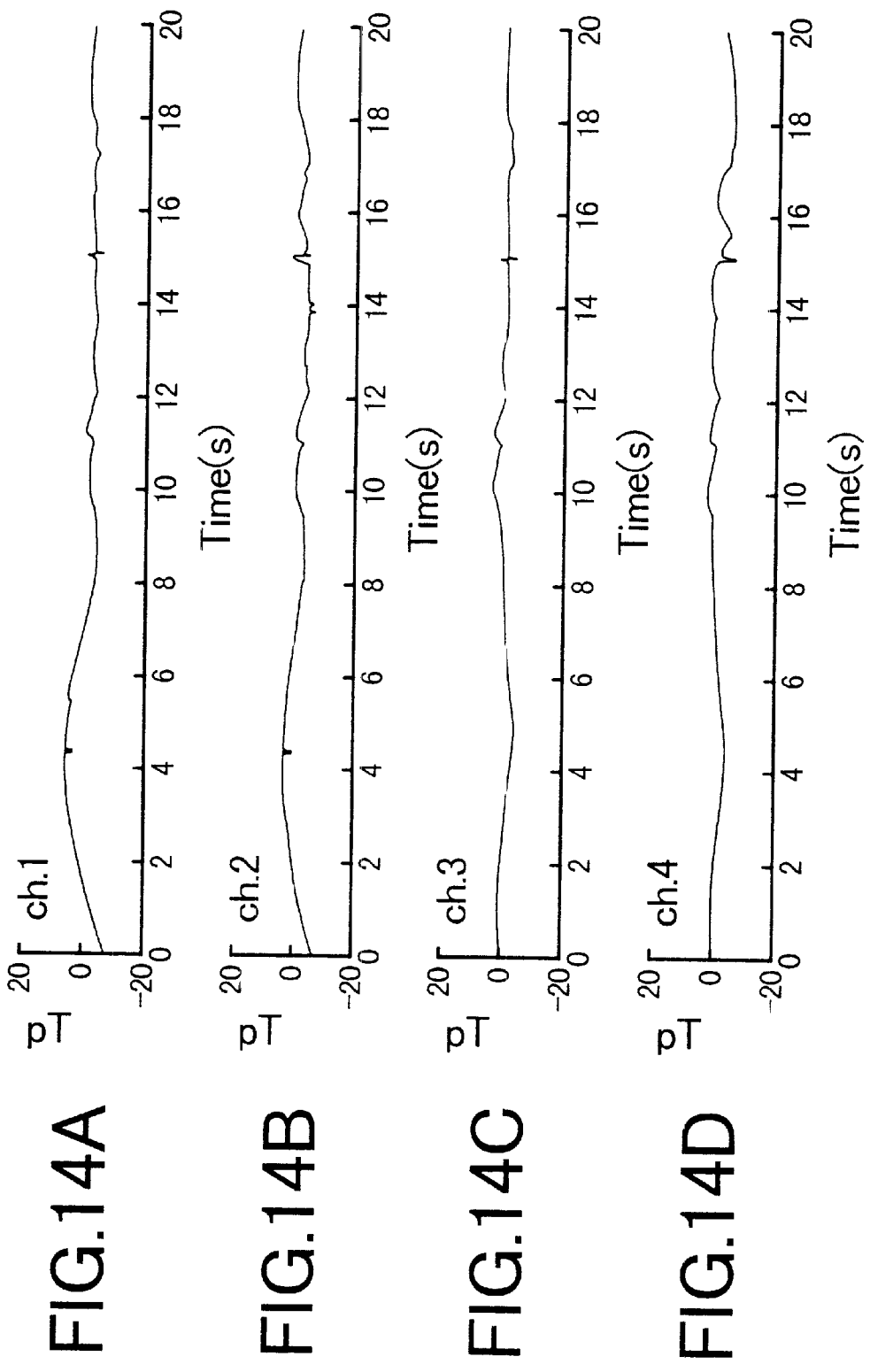

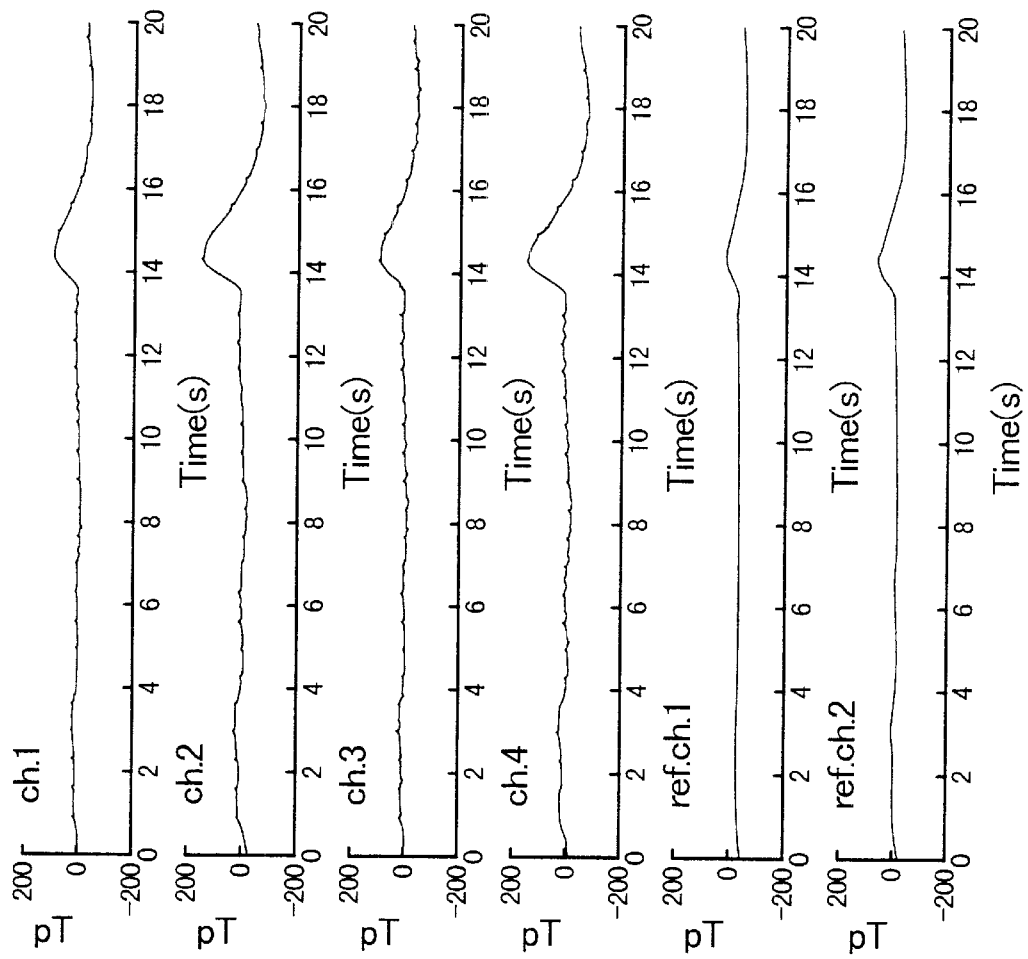

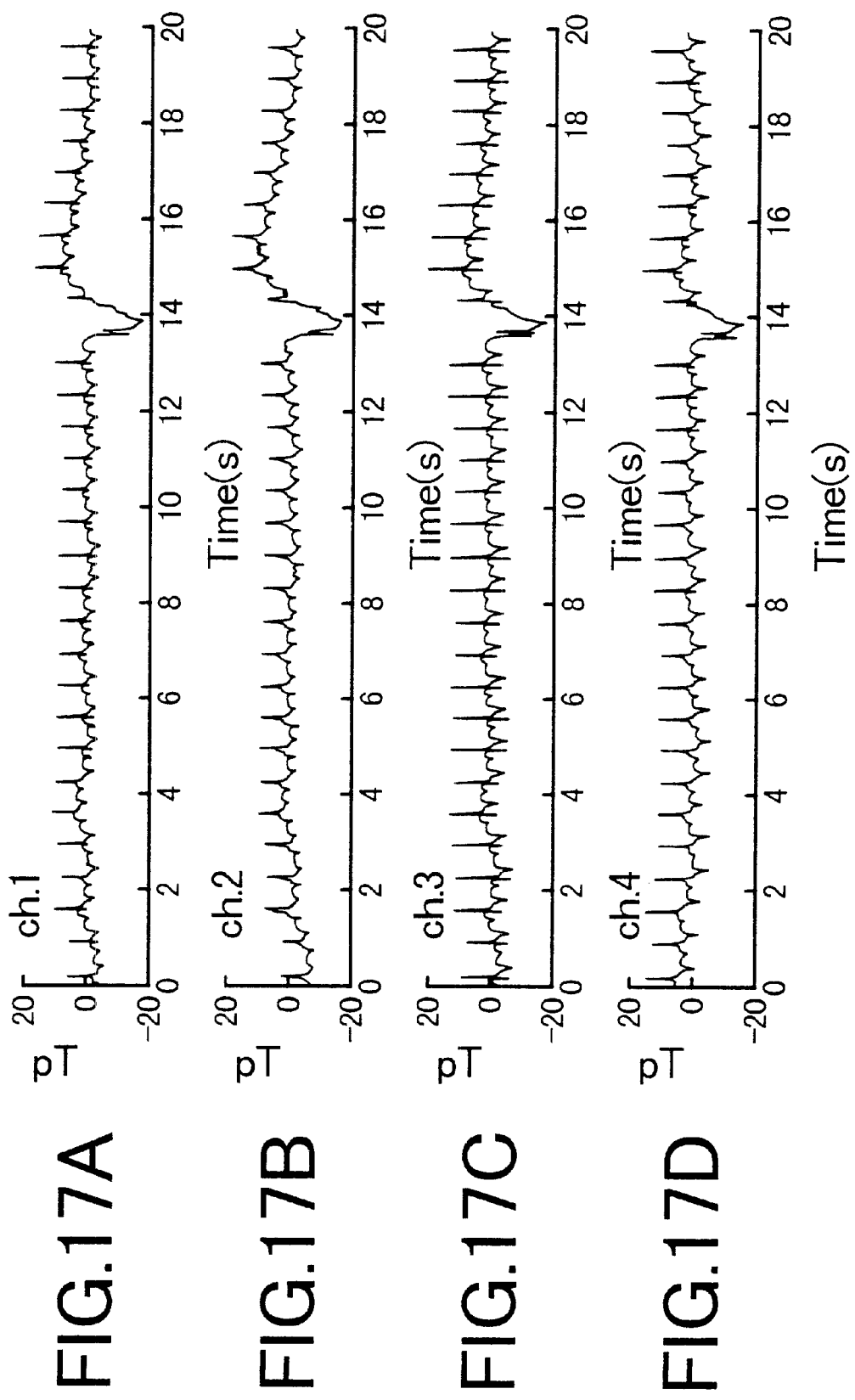

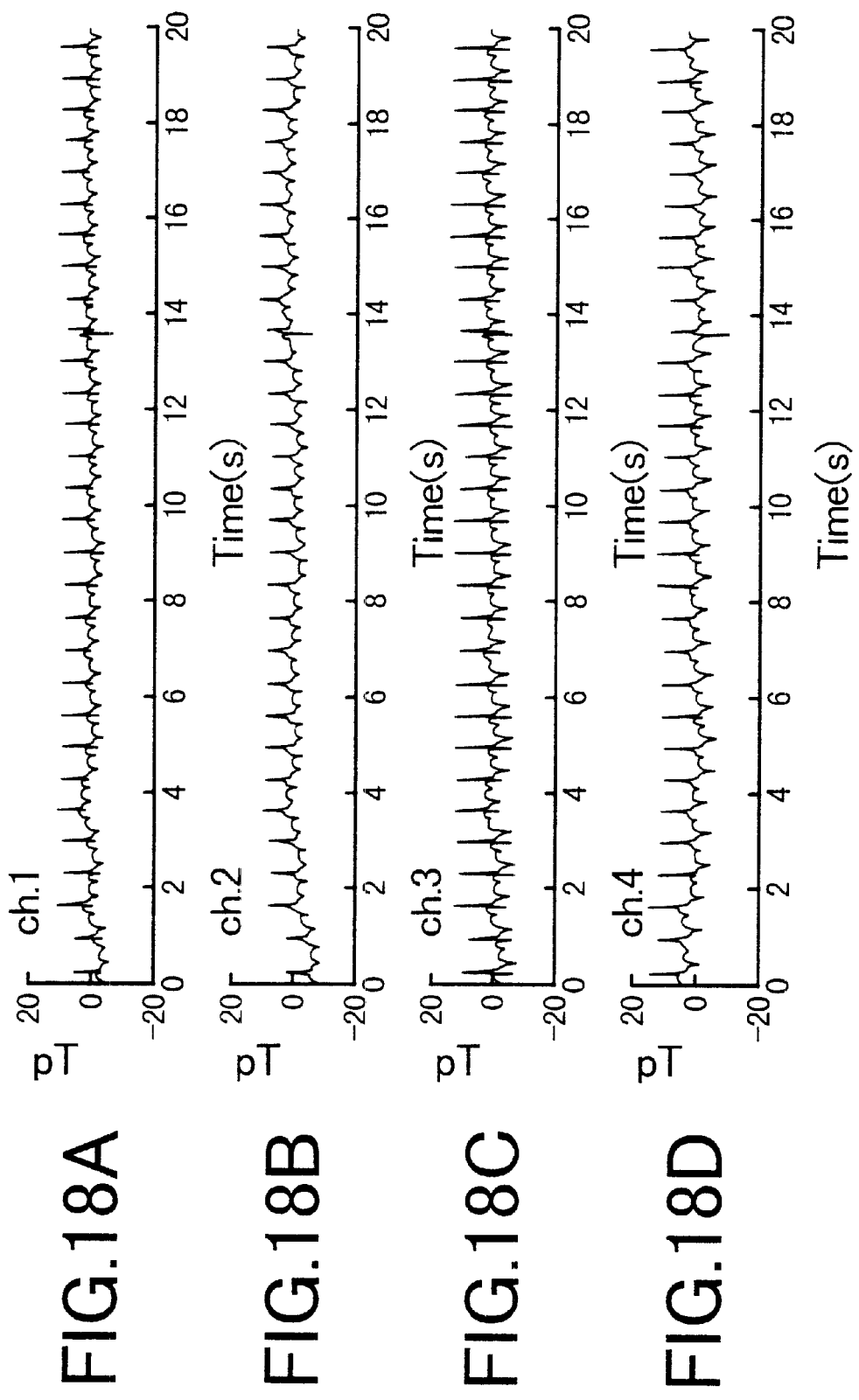

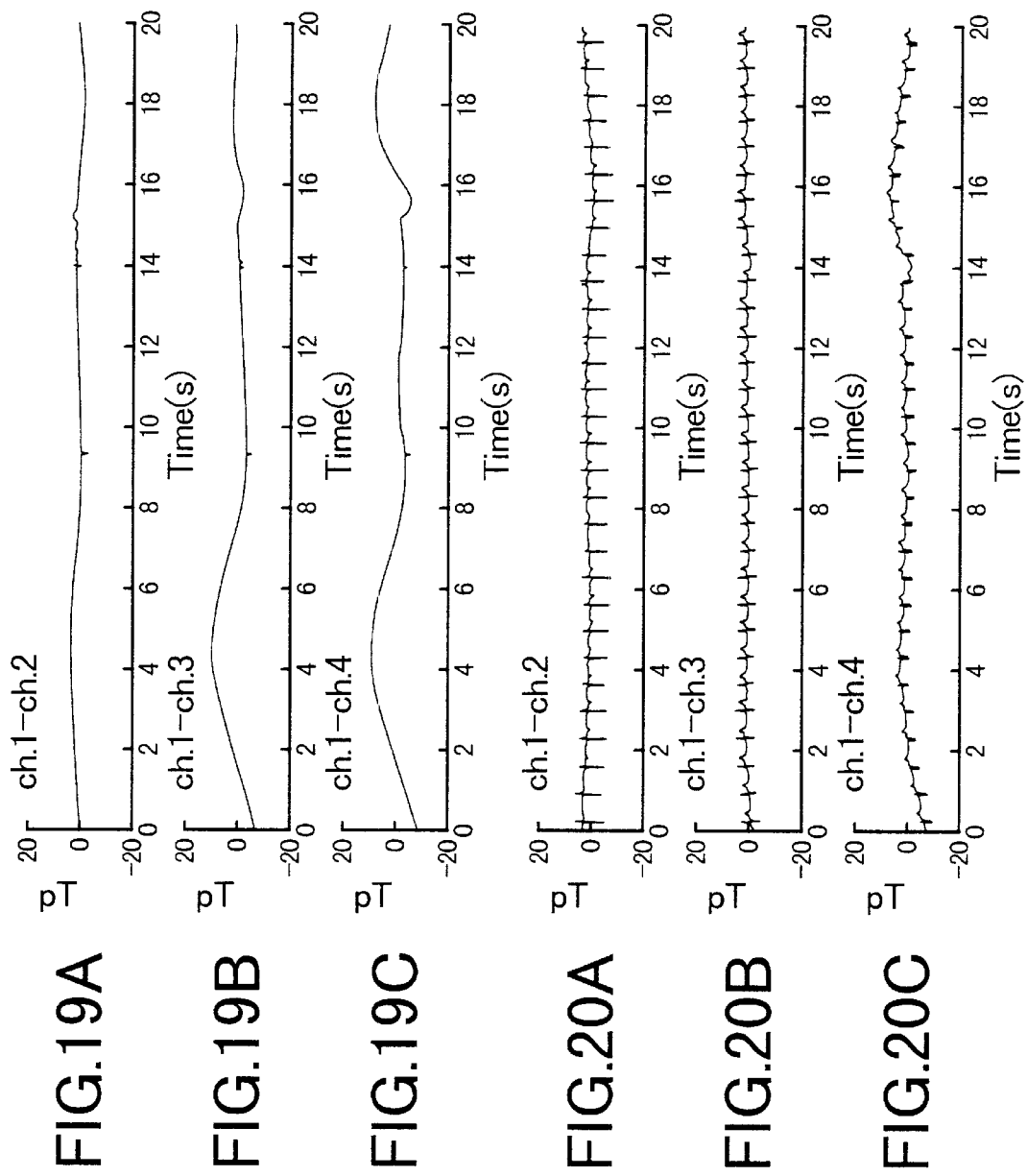

FIG.22

| channel | TIME CONSTANT | |
|---|---|---|
| | data1 | data2 |
| ch 1 | 0.22 | 0.26 |
| ch 2 | 0.25 | 0.32 |
| ch 3 | 0.21 | 0.23 |
| ch 4 | 0.16 | 0.15 |

MAGNETIC FIELD MEASURING APPARATUS WHICH ENABLES EXTERNAL MAGNETIC NOISE CANCELLATION

BACKGROUND OF THE INVENTION

1. Field of the Invention

The present invention relates to a magnetic field measuring apparatus using Superconducting Quantum Interference Device (SQUID) magnetometers (gradiometers) to sense extremely weak magnetic fields such as biomagnetic fields originating from a portion of a living body, e.g., heart, brain, etc., geomagnetism, and those involved in nondestructive testing, and particularly relates to such apparatus that achieves the cancellation of external magnetic noise that causes interference.

2. Description of Related Art

Magnetic field measuring apparatus using SQUID magnetometers (gradiometers) is applied to measurements of extremely weak magnetic fields in such a manner that magnetic fields in the brain, heart, etc. are measured in a magnetically shielded room featuring a rate of attenuating magnetic fields of 40 to 50 decibels (dB) or more. As a combination of pickup coils to sense biomagnetic fields, first-order gradiometers are often used that detect a differential signal occurring between a first one-turn pickup coil and a second coil wound in a direction opposite to the first coil. The first-order gradiometers are characterized in that they cancel external magnetic noise from a remote noise source, while can detect signals from a magnetic field generated in the vicinity of the object to be inspected, such as, heart, brain, etc., without causing significant cancellation, and therefore they can easily decrease the effect of the external magnetic noise. The first-order gradiometers generally attenuate uniform magnetic fields by about 40 to 50 dB.

The above-mentioned magnetically shielded room and gradiometers in combination can cancel external magnetic noise by about 80 to 100 dB or more. However, if a moving body such as an electric train or a motor vehicle passes rather near the magnetically shielded room, 50 to 100 meters away from the room, external magnetic noise several tens of times as large as a biomagnetic field originating from a living body may be observed. In order to cancel strong magnetic noise of this order, various methods have been attempted.

For example, a method has been proposed by which a flux-gate magnetometer is placed outside the magnetically shielded room and signals detected by it from a magnetic field are used to allow a feedback current to flow through compensating coils, or noise-canceling coils wound around the outside wall of the room, aiming at compensation to adjust the output of the flux-gate magnetometer theoretically to 0 (related art 1: Meas. Sci. Technol. Vol. 2, pp. 596–601 [1991]).

Another noise cancellation method by using SQUID sensors (high-order gradiometers) formed through software has been devised, wherein signals detected by reference sensor coils are used (related art 2: Clin. Phys. Physiol. Meas., Vol. 12, Suppl. B, pp. 81–86 [1991]). This method uses a low-order, hardware gradient detector which is then processed relative to a common reference system to form a higher-order gradient response, though the detail of the reference system is not stated.

Japanese Patent Prepublication No. Hei 11-47108 (related art 3) describes a biomagnetic field measuring apparatus for decreasing the error of environmental magnetic noise elimination due to the lost balance of the coils employed. According to this publication, the biomagnetic field measuring apparatus is summarized below. A plurality of coils that artificially generate an incoming magnetic field are installed in known position on, for example, the external spherical surface of a dewar. Driving current is allowed to flow through the coils to drive them. By using the values that the pickup coils detected as the strength of this magnetic field generated by the coils and the driving current value, the pickup coils sensitivities and their balance are measured with high accuracy. The biomagnetic measurements obtained from the values detected by the pickup coils are compensated with high accuracy for the effect of the lost coil balance. As a result, the error of environmental magnetic noise elimination caused by the lost balance of the coils is decreased and the accuracy of biomagnetic measurements is improved. In the vacuum adiabatic enclosure, a plurality of biomagnetic field measuring pickup coils that primarily measure biomagnetic fields are installed near the physical object to be inspected and a plurality of reference sensor coils that primarily measure environmental magnetic fields are installed farther than the pickup coils away from the object.

Japanese Patent Prepublication No. Hei 11-83965 (related art 4) describes a complex of an environmental noise canceling system and a magnetic measurement apparatus that enables highly precise measurement of extremely weak magnetic fields from the physical object of interest without being affected by environmental noise in different frequency bands. According to this publication, a plurality of SQUID gradiometers with different dynamic ranges and through rates sense different environmental magnetic fields with different field strengths in different frequency bands and measure electric signals corresponding to the sensed environmental magnetic fields. The noise canceling system can cancel noise of environmental magnetic fields with different field strengths in different frequency bands, by generating a magnetic field, through a pair of actively-shielded coils, in an opposite direction of environmental magnetic fields, based on addition electric signals obtained by adding all measured electric signals, or, by subtracting the addition electric signals from the magnetic signals measured by the SQUID gradiometers for magnetic measurement.

Japanese Patent Prepublication No. Hei 9-84777 (related art 5) describes a biomagnetic field measuring apparatus that can precisely probe a current dipole in deeper position among a plurality of current dipoles put together with one laid on top of another downward. According to this publication, the apparatus uses an array of pickup coils to detect magnetic flux originating from biomagnetic fields, the array formed by combining a plurality types of pickup coils that differ in gradient order or/and baseline.

Related art 1 aims at compensation to adjust the output of the flux-gate magnetometer placed outside the magnetically shielded room theoretically to 0 by flowing the feedback current through the compensating coils, or noise-canceling coils installed on the outside wall of the room. When this compensation method is applied to a multi-channel magnetic field measuring apparatus having SQUID magnetometers consisting of a plurality of differential-type pickup coils, or namely, first-order gradiometers, the coils of all channels may vary in the rate of noise cancellation. A problem arises that this variation of noise cancellation rate is difficult to rectify.

The document disclosing related art 2 simply describes the relevant data in a case where a magnetically shielded room is not used, but does not describe a specific configuration of the reference system using reference sensor coils.

SUMMARY OF THE INVENTION

An object of the present invention is to provide a magnetic field measuring apparatus that enables external magnetic noise cancellation with precision, allows for variation in the noise cancellation rate and baseline among the differential-type pickup coils employed to make the channels of a multi-channel magnetic field measuring apparatus when executing noise cancellation, and makes it possible to eliminate distorted magnetic signal waveforms induced by the frequency property of a magnetically shielded room in which the apparatus is installed.

Terminology used herein is explained below:

"Differential-type pickup coils" mean the coils constituting a first-order or second-order gradiometer.

(1) Providing differential type pickup coils constitute a first-order gradiometer:

(1.1) A "gradiometer for detection" (first SQUID gradiometer) is a first-order SQUID gradiometer that detects the component in Z direction of magnetic noise from an external magnetic field as well as the component in Z direction of a biomagnetic field originating from a living body.

(1.2) A "gradiometer for compensation" (second SQUID gradiometer) is a first-order SQUID gradiometer that detects the component in Z direction of magnetic noise from an external magnetic field.

(1.3) An "input coil of a gradiometer for detection" means a first coil of the coils constituting a first-order gradiometer employed as one of the gradiometers for detection, positioned the nearest to the physical object to be inspected.

(1.4) An "input coil of a gradiometer for compensation" means a first coil of the coils constituting a first-order gradiometer employed as one of the gradiometers for compensation, positioned the nearest to the physical object to be inspected.

(1.5) A "compensating coil of a gradiometer for detection" means a second coil whose base surface is parallel with the base surface of the first coil of the coils constituting a first-order gradiometer employed as one of the gradiometers for detection, positioned farther than the first coil away from the physical object to be inspected.

(1.6) A "compensating coil of a gradiometer for compensation" means a second coil whose base surface is parallel with the base surface of the first coil of the coils constituting a first-order gradiometer employed as one of the gradiometers for compensation, positioned farther than the first coil away from the physical object to be inspected.

(1.7) "Outputs of gradiometers for detection" mean the outputs from the first order gradiometers used as the gradiometers for detection.

(1.8) "Outputs of gradiometers for compensation" mean the outputs from the first order gradiometers used as the gradiometers for compensation.

(1.9) A "baseline of a gradiometer for detection" means the baseline of a first-order gradiometer employed as one of the gradiometers for detection and is a distance between the base surfaces of the first and second coils of the gradiometer.

(1.10) A "baseline of a gradiometer for compensation" means the baseline of a first-order gradiometer employed as one of the gradiometers for compensation and is a distance between the base surfaces of the first and second coils of the gradiometer.

(2) Providing differential type pickup coils constitute a second-order gradiometer:

(2.1) A "gradiometer for detection" (first SQUID gradiometer) is a second-order SQUID gradiometer that detects the component in Z direction of magnetic noise from an external magnetic field as well as the component in Z direction of a biomagnetic field originating from a living body.

(2.2) A "gradiometer for compensation" (second SQUID gradiometer) is a second-order SQUID gradiometer that detects the component in Z direction of magnetic noise from an external magnetic field.

(2.3) An "input coil of a gradiometer for detection" means a first coil of the coils constituting a second-order gradiometer employed as one of the gradiometers for detection, positioned the nearest to the physical object to be inspected.

(2.4) An "input coil of a gradiometer for compensation" means a first coil of the coils constituting a second-order gradiometer employed as one of the gradiometers for compensation, positioned the nearest to the physical object to be inspected.

(2.5) "Compensating coils of a gradiometer for detection" mean second, third, and fourth coils whose base surface is parallel with the base surface of the first coil of the coils constituting a second-order gradiometer employed as one of the gradiometers for detection, serially positioned in order farther than the first coil away from the physical object to be inspected. In the present invention, it is defined that the area of the second coil equals the area of the third coil.

(2.6) "Compensating coils of a gradiometer for compensation" mean second, third, and fourth coils whose base surface is parallel with the base surface of the first coil of the coils constituting a second-order gradiometer employed as one of the gradiometers for compensation, serially positioned in order farther than the first coil away from the physical object to be inspected. In the present invention, it is defined that the area of the second coil equals the area of the third coil.

(2.7) "Outputs of gradiometers for detection" mean the outputs from the second-order gradiometers used as the gradiometers for detection.

(2.8) "Outputs of gradiometers for compensation" mean the outputs from the second-order gradiometers used as the gradiometers for compensation.

(2.9) "Baselines of a gradiometer for detection" mean the baselines of a second-order gradiometer employed as one of the gradiometers for detection and are a distance between the base surfaces of the first and second coils and a distance between the base surfaces of the third and fourth coils of the gradiometer. In the present invention, it is defined that the distance between the base surfaces of the first and second coils equals the distance between the base surfaces of the third and fourth coils.

(2.10) "Baselines of a gradiometer for compensation" mean the baselines of a second-order gradiometer employed as one of the gradiometers for compensation and are a distance between the base surfaces of the first and second coils and a distance between the base surfaces of the third and fourth coils of the gradiometer.

In the present invention, it is defined that the distance between the base surfaces of the first and second coils equals the distance between the base surfaces of the third and fourth coils.

A magnetic field measuring apparatus of the present invention is configured in hardware to primarily comprise a plurality of SQUID gradiometers that consist of differential-type pickup coils (first-order gradiometers or second-order gradiometers) and detect external magnetic noise as well as magnetic fields originating from a living body and a single unit or a plurality of units of SQUID gradiometers (second SQUID gradiometers) that also consist of differential-type pickup coils (first-order gradiometers or second-order gradiometers) and detect external magnetic noise. These SQUID gradiometers are arranged in a cryostat that is filled with cryogenic refrigerants such as liquid helium, liquid nitrogen, or the like; alternatively, a refrigerator is installed in the cryostat. A gantry supports the cryostat.

The apparatus is further configured such that the differential-type pickup coil baseline of the second SQUID gradiometer(s) is shorter than that of the first SQUID gradiometers, which thereby prevents the second gradiometer(s) from detecting the magnetic fields originating from a living body's portion such as a heart.

By using mixed magnetic signals in which the external magnetic noise signals detected by the second SQUID gradiometer(s) are mixed with the biomagnetic signals and noise signals detected by the first SQUID gradiometers and applying the method of least squares, the apparatus computes an optimum fitting parameter and cancels (eliminates) the noise signals from the mixed magnetic signals detected (first method of canceling external magnetic noise).

The apparatus further eliminates the remaining external magnetic noise that it cannot cancel by the above first method of canceling external magnetic noise; in other words, the noise caused by the frequency property of a magnetically shielded room in which the apparatus is installed, through approximation of a theoretical waveform representing the noise whose magnetic field strength changes as a function of time, which is expressed by equation 1, and by calculating amplitude A and time constant T by the method of least squares.

$$B(t)=-A \cdot t^2 \cdot \exp(-t/T)$$ [Equation 1]

It should be noted that related arts 1, 2, 3, 4, and 5 disclose nothing corresponding to the features of the invention configured to: set the differential-type pickup coil baseline of the second SQUID gradiometer(s) for external magnetic noise detection shorter than that of the first SQUID gradiometers for biomagnetic detection; use a plurality of second SQUID gradiometers comprising differential-type pickup coils with different baselines; and cancel the external magnetic noise induced by the frequency property of the magnetically shielded room in which the apparatus is installed.

As a first configuration of the invention, a magnetic field measuring apparatus comprises a plurality of first SQUID gradiometers that detect signals in a normal direction of a magnetic field originating from a physical object to be inspected, a second SQUID gradiometer that detects signals in a normal direction of external magnetic noise, a cryogenic enclosure to keep the first and second SQUID gradiometers cold, a driving circuit to drive the first and second SQUID gradiometers, a computer that executes signal processing after collecting the signals detected by the first and second SQUID gradiometers, and a display means for displaying the results of signal processing. The magnetic field measuring apparatus is characterized in that the first and second SQUID gradiometers comprise differential-type pickup coils (to constitute first-order or second-order gradiometers), some of which are used as compensating coils, and the length of differential-type pickup coil baseline of second SQUID gradiometer is shorter than the length of differential-type pickup coil baselines of the first SQUID gradiometers.

In the first configuration of the invention, the magnetic field measuring apparatus is further characterized as follow.

(1) The apparatus placed in a magnetically shielded room detects the signals in a normal direction of a magnetic field originating from the physical object to be inspected and includes a signal unit or a plurality of units of second SQUID gradiometers. The computer executes first signal processing by using mixed magnetic signals in which the external magnetic noise signals detected by the second SQUID gradiometer(s) are mixed with biomagnetic signals and external magnetic noise signals detected by the first SQUID gradiometers and applying the method of least squares, thus canceling the external magnetic noise from the mixed magnetic signals. Moreover, the computer executes second signal processing in such a manner that the computer executes approximation of waveform B(t), which represents the waveform of external magnetic noise occurring due to the frequency property of the magnetically shielded room near the initial time at which such noise begins to occur, by using equation $B(t)=-A \cdot t^2 \cdot \exp(-t/T)$, where A is amplitude, T is time constant, and t is time variable, calculates amplitude A and time constant T, according to the method of least squares, by using the magnetic signal waveform obtained through the first processing, and cancels such noise from the magnetic signal waveform obtained through the first signal processing by using the waveform B(t) determined by the method of least squares.

(2) The computer infers the initial time and the inferred initial time is indicated on the time axis for showing a magnetic signal waveform from which the external magnetic noise has been canceled by the first and second signal processing.

(3) The input coil area of the differential-type pickup coils of the second SQUID gradiometer(s) is greater than the input coil area of the differential-type pickup coils of the first SQUID gradiometers.

As a second configuration of the invention, a magnetic field measuring apparatus comprises a plurality of first SQUID gradiometers that detect signals in a normal direction of a magnetic field originating from a physical object to be inspected within a magnetically shielded room, a second SQUID gradiometer that detects signals in a normal direction of external magnetic noise, a cryogenic enclosure to keep the first and second SQUID gradiometers cold, a driving circuit to drive the first and second SQUID gradiometers, a computer that executes signal processing after collecting the signals detected by the first and second SQUID gradiometers, and a display means for displaying the results of signal processing. The magnetic field measuring apparatus is characterized in that the first and second SQUID gradiometers comprise differential-type pickup coils (to constitute first-order or second-order gradiometers), some of which are used as compensating coils, the baseline length of the differential-type pickup coils of the second SQUID gradiometer is shorter than the baseline length of the differential-type pickup coils of the first SQUID gradiometers, and the computer executes signal processing (a) to cancel the external magnetic noise due to variant noise cancellation rates of the first SQUID gradiometers from the magnetic signal waveform in a normal direction obtained through detection by the first SQUID gradiometers and signal processing (b) to cancel the external magnetic noise occurring due to the frequency property of the magnetically shielded room from the magnetic signal waveform obtained through the signal processing (a).

In the second configuration of the invention, the magnetic field measuring-apparatus is further characterized in that:

(1) the computer infers initial time at which external magnetic noise begins to occur due to the frequency property of the magnetically shielded room and the inferred initial time is indicated on the time axis for showing a magnetic signal waveform from which the external magnetic noise has been canceled by signal processing (a) and (b); and (2) the input coil area of the differential-type pickup coils of the second SQUID gradiometer is greater than the input coil area of the differential-type pickup coils of the first SQUID gradiometers.

As a third configuration of the invention, a magnetic field measuring apparatus comprises a plurality of first SQUID gradiometers that detect signals in a normal direction of a magnetic field originating from a physical object to be inspected within a magnetically shielded room, second and third SQUID gradiometers that detect signals in a normal direction of external magnetic noise, a cryogenic enclosure to keep the first, second, and third SQUID gradiometers cold, a driving circuit to drive the first, second, and third SQUID gradiometers, a computer that executes signal processing after collecting the signals detected by the first, second, and third SQUID gradiometers, and a display means for displaying the results of signal processing. The magnetic field measuring apparatus is characterized in that the first, second, and third SQUID gradiometers comprise differential-type pickup coils (to constitute first-order or second-order gradiometers), some of which are used as compensating coils, the baseline lengths of the differential-type pickup coils of the second and third SQUID gradiometers are shorter than the baseline length of the differential-type pickup coils of the first SQUID gradiometers, the baseline length of the differential-type pickup coils of the second SQUID gradiometer is shorter than the baseline length of the differential-type pickup coils of the third SQUID gradiometer, and the computer executes signal processing (a) to cancel the external magnetic noise due to variant noise cancellation rates of the first SQUID gradiometers from the magnetic signal waveform in a normal direction obtained through detection by the first SQUID gradiometers, signal processing (b) to cancel the external magnetic noise due to that the baseline of the differential-type pickup coils of the second SQUID gradiometer differs from the baseline of the differential-type pickup coils of the third SQUID gradiometer from the magnetic signal waveform obtained through the signal processing (a), and signal processing (c) to cancel the external magnetic noise occurring due to the frequency property of the magnetically shielded room from the magnetic signal waveform obtained through the signal processing (b).

In the third configuration of the invention, the magnetic field measuring apparatus is further characterized in that:

(1) the computer infers initial time at which external magnetic noise begins to occur due to the frequency property of the magnetically shielded room and the inferred initial time is indicated on the time axis for showing a magnetic signal waveform from which the external magnetic noise has been canceled by signal processing (a), (b), and (c); and (2) the input coil area of the differential-type pickup coils of the second and third SQUID gradiometers is greater than the input coil area of the differential-type pickup coils of the first SQUID gradiometers.

As a fourth configuration of the invention, a magnetic field measuring apparatus comprises a plurality of first SQUID gradiometers that detect signals in a normal direction of a magnetic field originating from a physical object to be inspected within a magnetically shielded room which blocks out high-frequency electromagnetic waves, a plurality of second SQUID gradiometers that detect signals in a normal direction of external magnetic noise, a cryogenic enclosure to keep the first and second SQUID gradiometers cold, a driving circuit to drive the first and second SQUID gradiometers, noise-canceling coils positioned over and under the physical object to be inspected to generate a normal-directional magnetic field that cancels the external magnetic noise, a control means for controlling the current flowing through the noise-canceling coils, and a computer that executes signal processing after collecting the signals detected by the first and second SQUID gradiometers. The magnetic field measuring apparatus is characterized in that the first and second SQUID gradiometers comprise differential-type pickup coils (to constitute first-order or second-order gradiometers), some of which are used as compensating coils, the baseline length of the differential-type pickup coils of the second SQUID gradiometers is shorter than the baseline length of the differential-type pickup coils of the first SQUID gradiometers, the control means controls the current flowing through the noise-canceling coils on the basis of the output from one of the second SQUID gradiometers, and the noise-canceling coils generate a normal-directional magnetic field that exerts force in a direction opposite to the external magnetic noise.

In the fourth configuration of the invention, the magnetic field measuring apparatus is further characterized in that:

(1) the input coil area of the differential-type pickup coils of the second SQUID gradiometers is greater than the input coil area of the differential-type pickup coils of the first SQUID gradiometers.

(2) a separate driving circuit is provided to drive one of the second SQUID gradiometers and the noise-canceling coils also serve as feedback coils to be used in the separate drive circuit.

(3) the noise-canceling coils are placed inside or outside the magnetically shielded room.

As a fifth configuration of the invention, a magnetic field measuring apparatus comprises a plurality of first SQUID gradiometers that detect signals in a predetermined direction or a combination of predetermined directions of a magnetic field originating from a physical object to be inspected, a second SQUID gradiometer that detects signals in a predetermined direction or a combination of predetermined directions of external magnetic noise, a cryogenic enclosure to keep the first and second SQUID gradiometers cold, a driving circuit to drive the first and second SQUID gradiometers, a computer that executes signal processing after collecting the signals detected by the first and second SQUID gradiometers, and a display means for displaying the results of signal processing. The magnetic field measuring apparatus is characterized in that the first and second SQUID gradiometers comprise differential-type pickup coils and the baseline length of the differential-type pickup coils of the second SQUID gradiometer is shorter than the baseline length of the differential-type pickup coils of the first SQUID gradiometers.

In the fifth configuration of the invention, a predetermined direction or a combination of predetermined directions is defined as at least any one of the x, y, and z directions. Besides, the predetermined direction or the combination of predetermined directions includes a normal direction or/and a tangential direction. The apparatus in the fifth configuration detects signals of normal or/and tangential directional components of a magnetic field originating from the object to be inspected and executes signal processing to cancel the external magnetic noise in normal or/and tangential directions.

With reference to FIG. 1, a typical configuration of the invention is summarized below. The apparatus configured as in FIG. 1 primarily comprises a plurality of first SQUID gradiometers 9 that detect signals of a biomagnetic field and external magnetic noise, a plurality of second SQUID gradiometers 10 that detect signals of external magnetic noise, a driving circuit 6 to drive the first and second SQUID gradiometers, a computer 8 that executes signal processing after collecting the signals detected by the first and second SQUID gradiometers. The first and second SQUID gradiometers comprise differential-type pickup coils to constitute first-order gradiometers. The baselines of the coils of first-order gradiometers of the second SQUID gradiometers are shorter than that of the first SQUID gradiometers. From the detected biomagnetic signal waveforms, the apparatus executes processing to cancel external magnetic noise that exists there due to the following: the coils of first-order gradiometers of the first SQUID gradiometers give variant noise cancellation rates; the baselines formed by the coils of the first-order gradiometers of the second SQUID gradiometers differ, and noise is induced by the frequency properties of the magnetically shielded room in which the apparatus is installed. The invention in this configuration can provide a magnetic field measuring device that can exactly cancel even spiky and considerably strong environmental noise.

According to the invention that can be configured in several ways described above, the SQUID gradiometers for detecting signals in a normal direction of a magnetic field originating from a living body detects biomagnetic signals into which some external magnetic noise in a normal direction is mixed, and from which normal-directional biomagnetic signals can be separated and extracted through the use of the normal-directional external magnetic noise signals detected by the SQUID gradiometer(s) for detecting external magnetic noise.

Furthermore, distorted magnetic signal waveforms in a normal direction, induced by the frequency property of the magnetically shielded room in which the apparatus is installed can be eliminated by using a theoretical equation.

According to the invention that can be configured in several ways, a biomagnetic field measuring apparatus can be made to enable sensitive measurement of an extremely weak magnetic field originating from the physical object to be inspected, for example, a human's heart, even an unborn baby's heart in the mother's body.

According to the invention, variant noise cancellation rates for uniform magnetic fields of differential-type pickup coils to constitute SQUID gradiometers and different baselines formed by these coils are taken into consideration when external magnetic noise is canceled, and therefore noise can be canceled precisely.

A magnetic field measuring apparatus offered by the invention can exactly execute the cancellation of external magnetic noise due to the frequency property of a magnetically shielded room in which the apparatus is installed and can precisely cancel even spiky and considerably strong environmental noise.

Furthermore, the invention can offer a biomagnetic field measuring apparatus enabling sensitive measurement of an extremely weak magnetic field originating from a physical object to be inspected, for example, a human's heart, even an unborn baby's heart in the mother's body.

BRIEF DESCRIPTION OF THE DRAWINGS

Other objects and advantages of the invention will become apparent during the following discussion of the accompanying drawings, wherein:

FIG. 9 shows a sample magnetic signal waveform measured by the flux-gate magnetometer included in the magnetic field measuring apparatus of Embodiment 2;

FIG. 12 shows samples of magnetic signal waveforms after external magnetic noise is canceled from the magnetic signal waveforms shown in FIG. 11 by using the first gradiometer for compensation included in Embodiment 1 (according to the procedure shown in FIG. 4);

FIG. 14 shows samples of magnetic signal waveforms after the external magnetic noise occurring due to the frequency property of the magnetically shielded room is canceled from the magnetic signal waveforms shown in FIG. 13 (according to the procedure shown in FIG. 7);

FIG. 15 shows samples of magnetic signal waveforms measured by the SQUID gradiometers of the magnetic field measuring apparatus of Embodiment 2 during the measurement of a magnetic field originating from the object to be inspected that is a heart;

FIG. 17 shows samples of magnetic signal waveforms after external magnetic noise is canceled from the waveforms shown in FIG. 16 by using the second gradiometer for compensation included in Embodiment 1 (according to the procedure shown in FIG. 5);

FIG. 18 shows samples of magnetic signal waveforms after the external magnetic noise occurring due to the frequency property of the magnetically shielded room is canceled from the magnetic signal waveforms shown in FIG. 17 (according to the procedure shown in FIG. 7);

FIG. 19 shows samples of magnetic signal waveforms after inter-channel differential processing is applied to the waveforms shown in FIG. 13;

FIG. 20 shows samples of magnetic signal waveforms after inter-channel differential processing is applied to the waveforms shown in FIG. 17;

FIG. 22 shows a list of the time constants obtained from the respective waveforms shown in FIGS. 13 and 17 in Embodiment 2;

DETAILED DESCRIPTION OF THE PREFERRED EMBODIMENTS

Based on relevant Figs., preferred embodiments of the present invention will be explained in detail below. The preferred embodiments will be detailed herein on the assumption that first-order gradiometers made up of differential-type pickup coils are used. However, the invention can apply to cases where second-order gradiometers made up of differential-type pickup coils are used, as will be detailed later.

Embodiment 1

Figure 1:
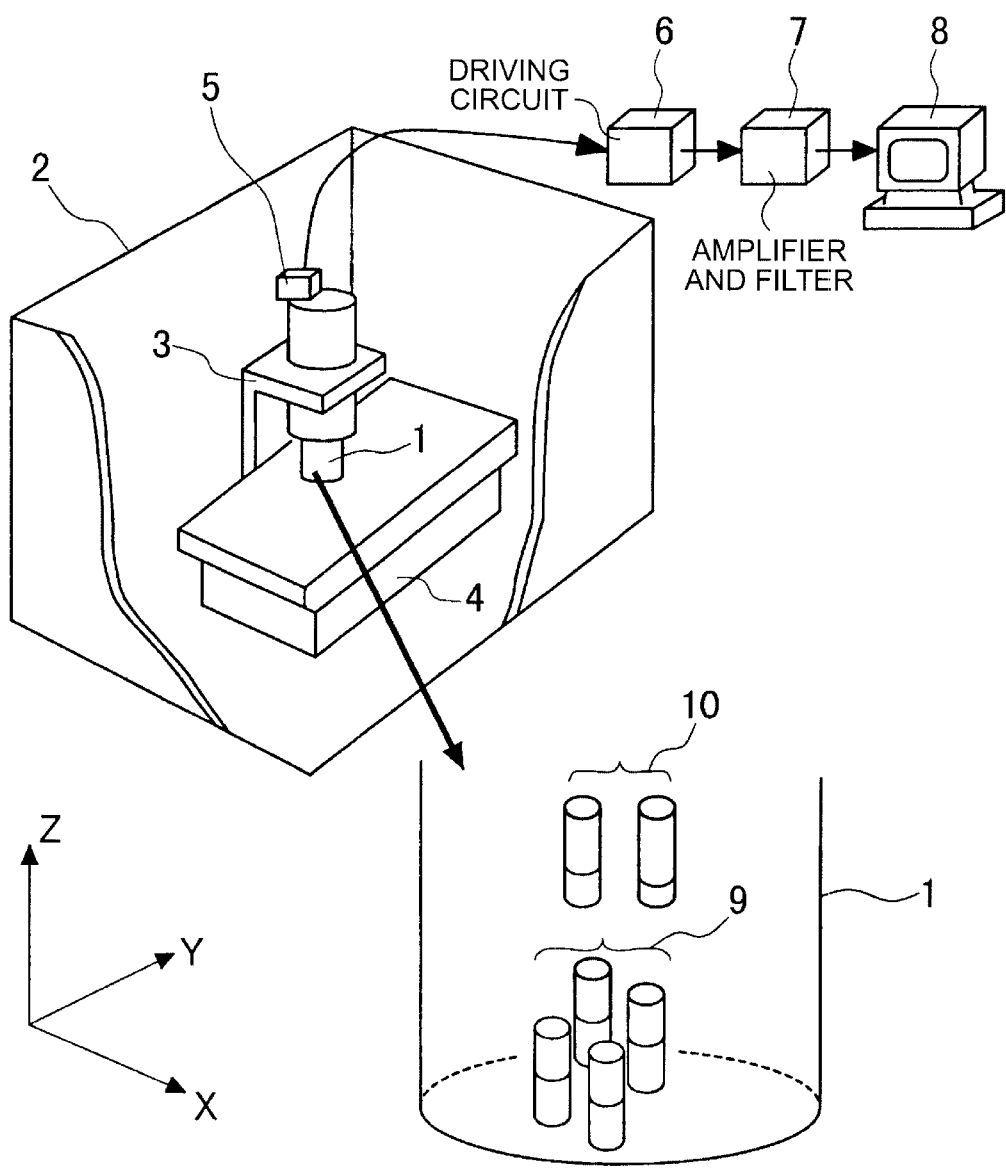
FIG. 1 is a schematic illustration showing an example of the configuration of a magnetic field measuring apparatus according to a preferred Embodiment 1 of the present invention.

FIG. 1 is a schematic illustration showing an example of the configuration of a magnetic field measuring apparatus according to a preferred Embodiment 1 of the present invention. In a magnetically shielded room 2, a bed 4 on which a physical object such as a human body to be inspected rests and a gantry that supports a cryostat (dewar) 1 are placed. In the internal space of the cryostat 1, at the bottom, four gradiometers for detection 9 are arranged in an array of 2×2. Above the gradiometers for detection 9, two gradiometers for compensation 10 are positioned on a same level. The structure of the gradiometers for detection 9 and the gradiometers for compensation 10 will be explained in detail later with FIG. 2.

The gradiometers for detection 9 and the gradiometers for compensation 10 are driven by a driving circuit 6 via a connector 5 and their outputs are amplified and filtered by an amplifying and filtering unit 7 and eventually collected to a computer 8. The computer 8 executes external magnetic noise cancellation, which will be detailed later, for the outputs from the gradiometers for detection 9, using the output signals from the gradiometers for compensation 10, executes signal processing such as inferring an average magnetic field and analyzing a magnetic field distribution, and displays the results of processing on a display.

Figure 2:
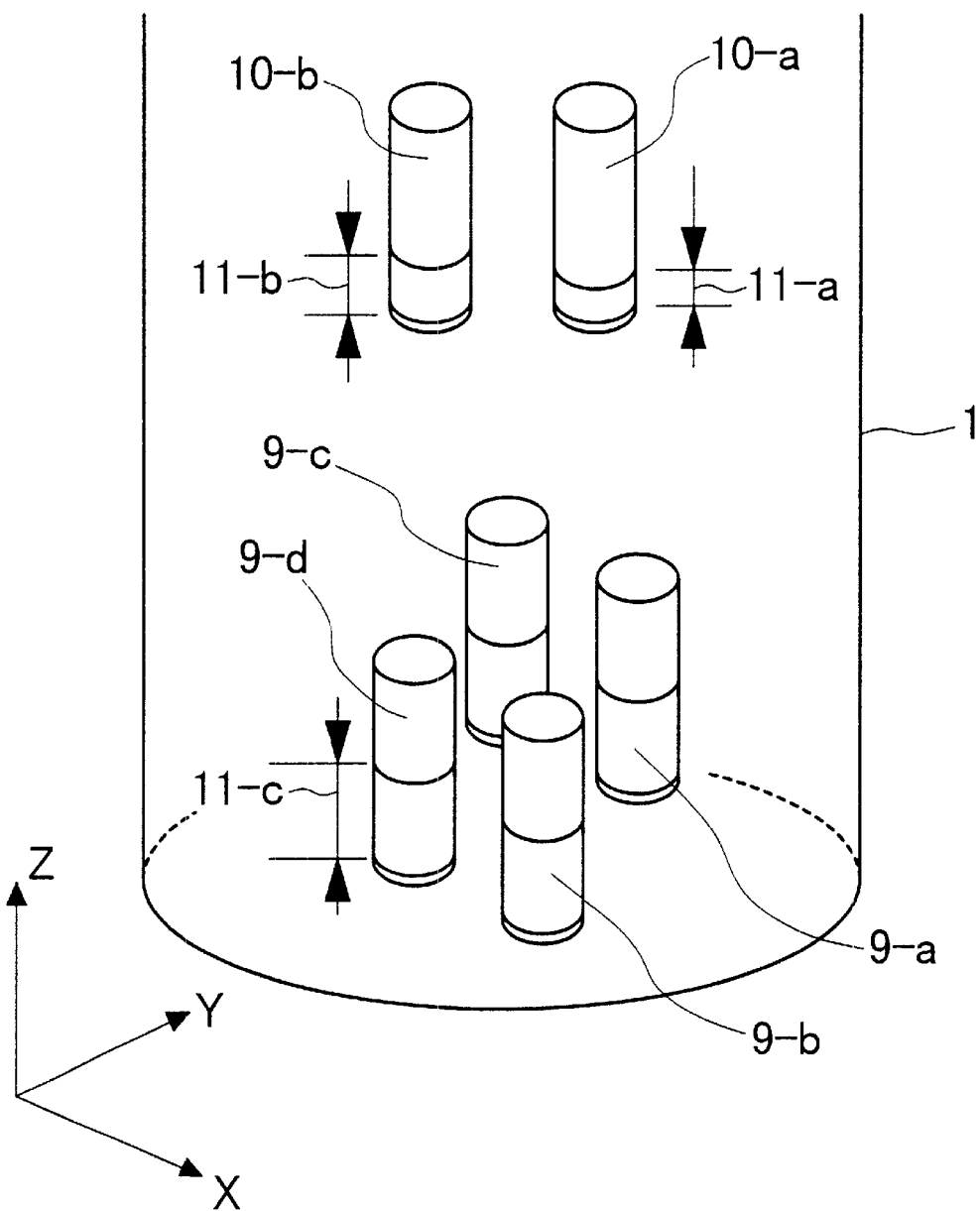
FIG. 2 is a schematic illustration showing an example of the structure of the gradiometers for detection and the gradiometers for compensation in Embodiment 1 of the invention.

FIG. 2 is a schematic illustration showing an example of the structure of the gradiometers for detection and the gradiometers for compensation in Embodiment 1 of the invention. This illustration is an enlarged view of the gradiometers for detection 9 to detect a biomagnetic field in the z direction and the gradiometers for compensation arranged in the cryostat 1. The baselines 11-$c$ of the gradiometers for detection, 9-$a$, 9-$b$, 9-$c$, and 9-$d$ are 50 mm. The gradiometers for detection, 9-$a$, 9-$b$, 9-$c$, and 9-$d$ are arranged to form a matrix of 2×2. The number of the gradiometers for detection and how they are arranged are not limited to the example shown in FIG. 2. More gradiometers for detection expanded to 9 to 64 units may be arranged to form a larger matrix, e.g., 3×3 to 8×8, or arranged in a three-dimensional structure. Besides, the length of the baselines 11-$c$ is not limited to 50 mm; 40 mm or the like is acceptable.

The baselines 11-$a$ and 11-$b$ of the gradiometers for compensation 10-$a$ and 10-$b$ are set shorter than the baselines 11-$c$ of the gradiometers for detection 9-$a$, 9-$b$, 9-$c$, and 9-$d$. In Embodiment 1, the baseline 11-$a$ is 10 mm and the baseline 11-$b$ is 30 mm. By making the baselines 11-$a$ and 11-$b$ of the gradiometers for compensation 10 (10-$a$ and 10-$b$) shorter than the baselines 11-$c$ of the gradiometers for detection 9 (9-$a$, 9-$b$, 9-$c$, and 9-$d$), the gradiometers for compensation 10 are designed to substantially detect only external magnetic noise without being affected by a magnetic field originating from the object, such as a heart, to be inspected.

In the arrangement of the gradiometers of Embodiment 1, there is a separation of 300 mm in the z direction between the base surfaces of the input coils of the gradiometers for detection 9 and the base surfaces of the input coils of the gradiometers for compensation 10. Not limited to 300 mm, this separation may be set at any distance enough to prevent a magnetic field that originates from the object, such as a heart, to be inspected a heart from affecting the measurement of the gradiometers for compensation 10.

On the assumption that the gantry 3 to support the cryostat 1 is placed in the magnetically shielded room not having the frequency property, the methods of external magnetic noise cancellation will be explained below.

Figure 3:
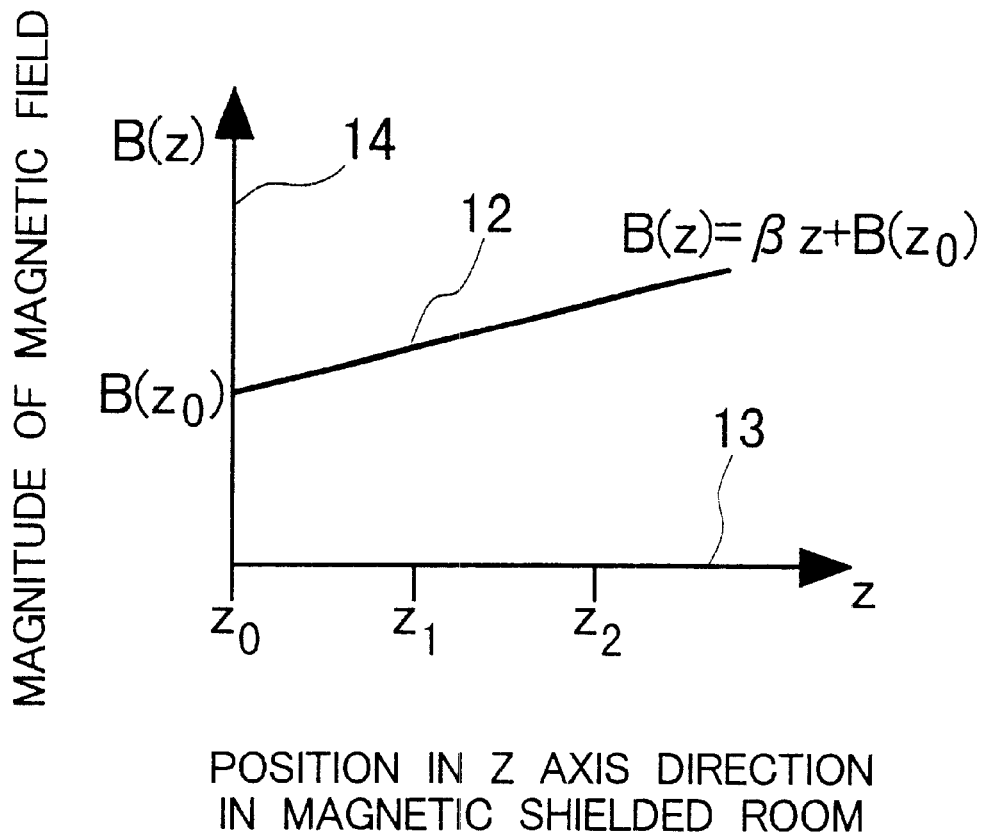
FIG. 3 is a graph showing the gradient of a magnetic field measured in the magnetically shielded room in Embodiment 1 of the invention.

FIG. 3 is a graph showing the gradient of a magnetic field measured in the magnetically shielded room in Embodiment 1 of the invention. The gradient of magnetic field is considered as the consequence that the magnetic field strength linearly changes in the z direction, which is expressed by equation 2. The coordinate axes (x, y, z) are as shown in FIGS. 1 and 2 and the coordinate points (x, y, $z_0$) are on the bottom surface of the cryostat.

$$B(z)=\beta z+B(z_0) \qquad \text{[Equation 2]}$$

For a gradiometer made up of the coils of first-order gradiometer, when input coil area is assumed to be $S_1$, compensation coil area $S_2$, and baseline d, magnetic flux $\Phi$ detected by the gradiometer will be expressed by equation 3. Here, the input coil area is positioned at z=z1 and the compensating coil area is positioned at $z=z_2=z_1+d$.

$$\Phi=S_1\times B(Z_1)-S_2\times B(Z_1+d)=S_1\times\{\beta\times z_1+b(z_0)\}-S_2\times\{\beta\times(z_1+d)+B(z_0)\}=$$
$$\beta\times(S_1-S_2)\times z_1+(S_1-S_2)\times B(z_0)-S_2\times\beta\times d \qquad \text{[Equation 3]}$$

If $\alpha$ is defined as will be expressed by equation 4, $B_0=\Phi/S_1$ is calculated by equation 5.

$$\alpha=S_2/S_1 \qquad \text{[Equation 4]}$$

$$B_0=\Phi/S_1=\beta\times(1-\alpha)\times z_1+(1-\alpha)\times B(z_0)-\alpha\times\beta\times d \qquad \text{[Equation 5]}$$

Here, a value of $(1-\alpha)$ represents a noise cancellation rate for an uniform magnetic field of the coils of a first-order gradiometer. If the magnetic field distribution in the space in which the gradiometers for detection and the gradiometers for compensation are arranged is as expressed by equation 2, the calculation of a magnetic field to be detected includes terms dependent on a coefficient of noise cancellation rate $(1-\alpha)$ and a term dependent on a coefficient of baseline d, as apparent from equation 5.

If the length of the baselines 11-c of the gradiometers of for detection 9 equals to the length of the baselines 11-a and 11-b of the gradiometers for compensation 10-a and 10-b, it is conceived that there remain only the terms dependent on a coefficient of noise cancellation rate $(1-\alpha)$ when the outputs from the gradiometers for detection 9 are compensated through the use of the outputs from the gradiometers for compensation 10 in a manner that will be explained later with FIGS. 4 and 5. However, even if the gradiometers for compensation 10 are placed 300 mm apart from the gradiometers for detection 9 and a magnetic field originating from the object such as a heart is measured, if the gradiometers for compensation 10 have a baseline of 50 mm, the waveform of the magnetic signals from the object significantly appears in the magnetic field detected by the gradiometers for compensation. As a result, the gradiometers for compensation 10 cannot detect only external magnetic noise because they are affected by the magnetic field originating from the object.

Therefore, the baselines 11-a and 11-b of the gradiometers for compensation 10 (10-a and 10-b) are set shorter than the baselines 11-c of the gradiometers for detection 9 and the baseline 11-a and the baseline 11-b are set at different lengths in order to prevent the gradiometers for compensation from being affected by the magnetic field originating from the object.

In the example shown in FIG. 2, for example, the baseline 11-a is 10 mm and the baseline 11-b is 30 mm. By arranging a plurality of gradiometers for compensation 10 having different baseline lengths, the detected magnetic field originating from the object can be compensated for different quantity of external magnetic noise mixed into it due to that the baselines of the gradiometers for detection 9 and the baselines of the gradiometers for compensation 10 differ in length.

Figure 4:
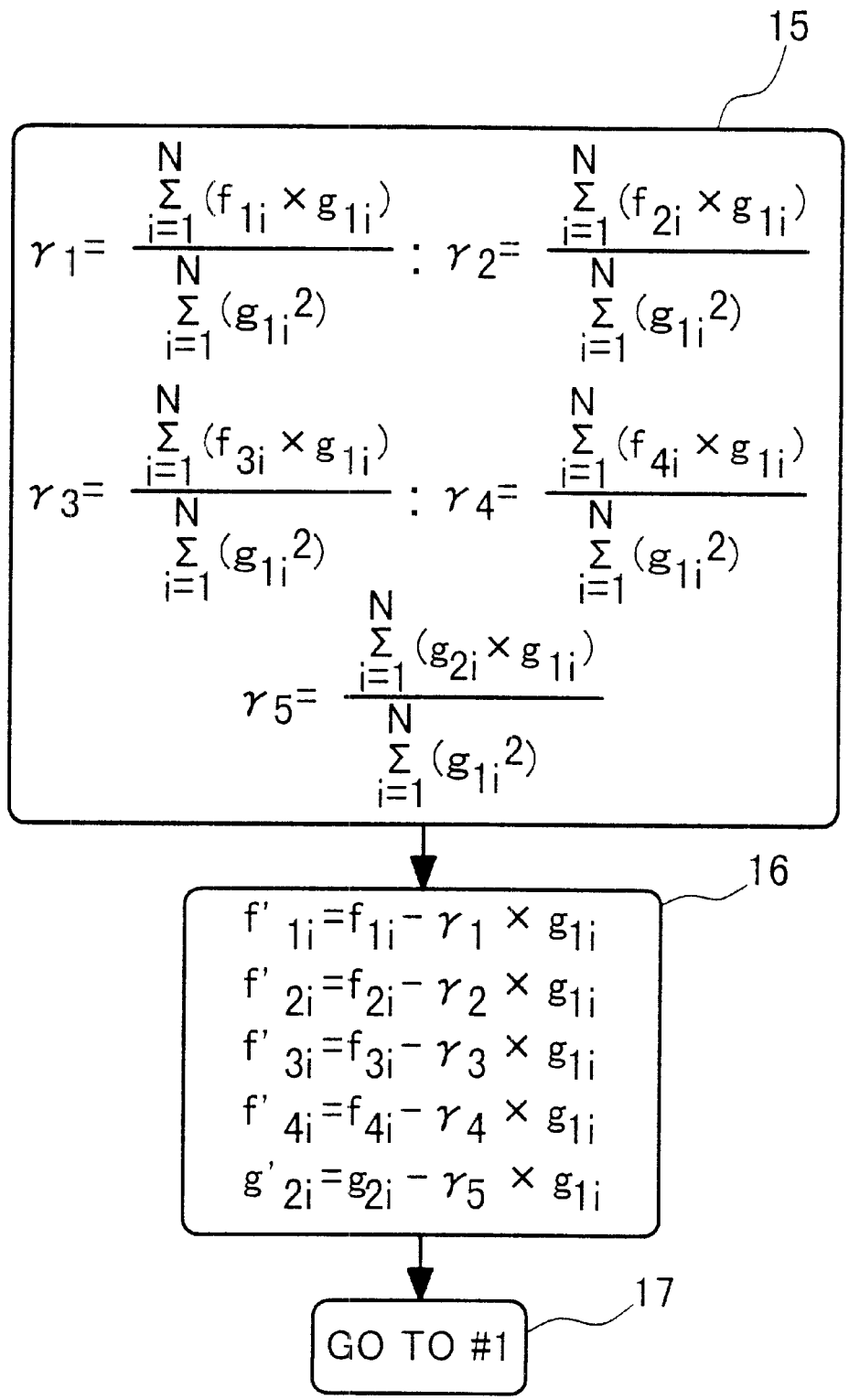
FIG. 4 is a flowchart diagram representing an example of how to cancel external magnetic noise by using a first gradiometer for compensation included in Embodiment 1.
Figure 5:
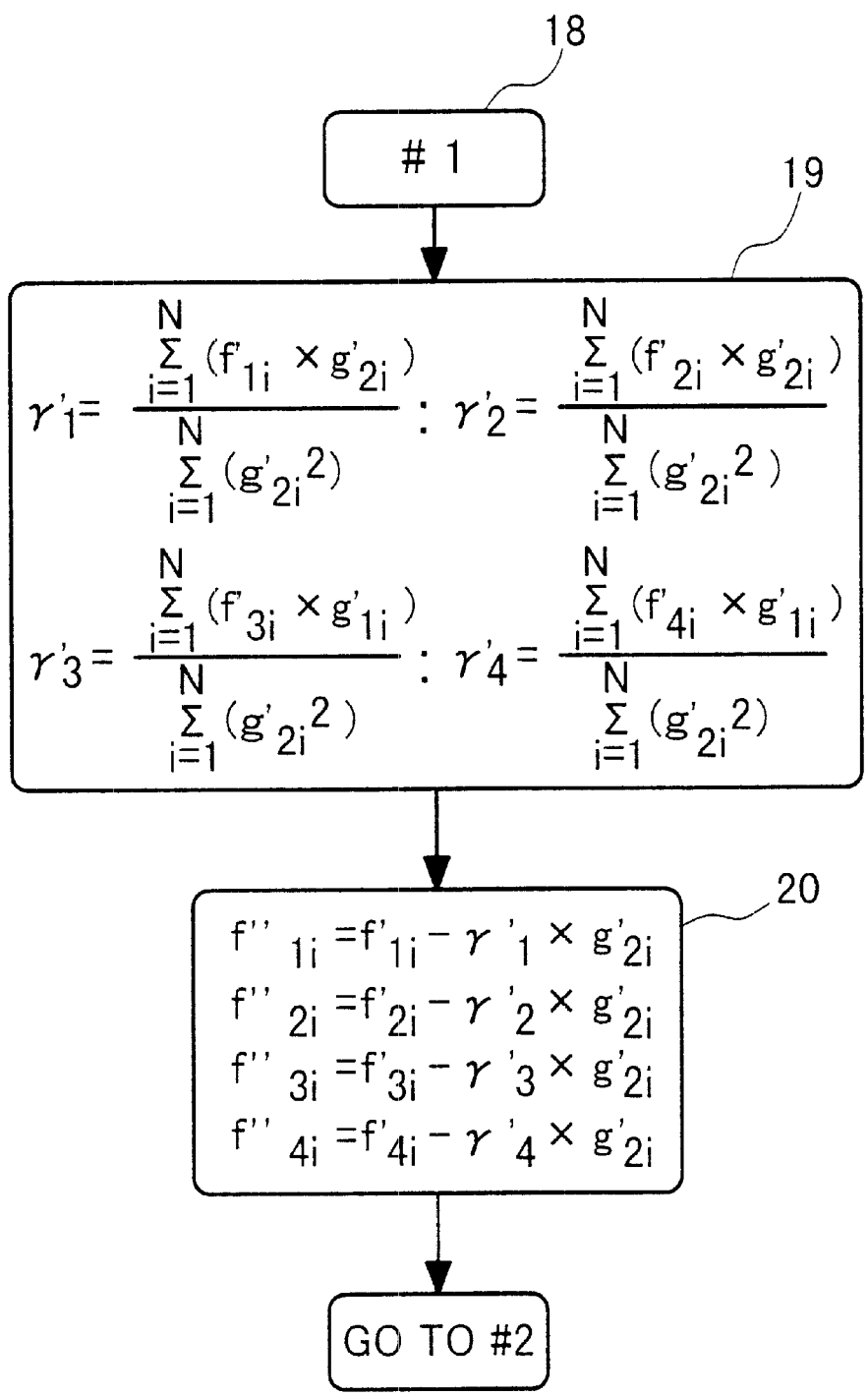
FIG. 5 is a flowchart diagram representing an example of how to cancel external magnetic noise by using a second gradiometer for compensation included in Embodiment 1.

With reference to FIGS. 4 and 5, a method of external noise cancellation (first method) by using the magnetic signal waveforms measured by the gradiometers for compensation will be explained below. FIG. 4 is a flowchart diagram representing an example of how to cancel external magnetic noise by using a first gradiometer for compensation included in Embodiment 1. FIG. 5 is a flowchart diagram representing an example of how to cancel external magnetic noise by using a second gradiometer for compensation included in Embodiment 1.

Here, $F_{1i}$, $F_{2i}$, $F_{3i}$, and $F_{4i}$ respectively represent the magnetic signal waveforms detected by the gradiometers for detection 9-a, 9-b, 9-c, and 9-d shown in FIG. 1 or FIG. 2 and $G_{1i}$ and $G_{2i}$ respectively represent the magnetic signal waveforms detected by the gradiometers for compensation 10-a and 10-b shown in FIG. 1 or FIG. 2. Assuming j=1~4 and k=1~2, $f_{1i}$, $f_{2i}$, $f_{3i}$, and $f_{4i}$ shown in FIGS. 4 and 5 are averaged and $g_{1i}$, and $g_{2i}$ shown in FIGS. 4 and 5 are averaged and each average is subtracted from each magnetic signal waveform, as will be expressed by equations 6 through 9. In the following equations, addition symbol $\Sigma$ expresses addition for i=1~=N (N is the number of sampling points on the time axis for the magnetic signal waveforms).

$$F_{j0}=\Sigma(F_{ji})/N \qquad \text{[Equation 6]}$$

$$G_{k0}=\Sigma(G_{ki})/N \qquad \text{[Equation 7]}$$

$$f_{ji}=F_{ji}-F_{j0} \qquad \text{[Equation 8]}$$

$$g_{ki}=G_{ki}-G_{k0} \qquad \text{[Equation 9]}$$

A value of $\gamma$ shown in FIG. 4 (process 15) and a value of $\gamma'$ shown in FIG. 5 can be determined by the method of least squares. The magnetic signal waveforms $f_{ji}$ (j=1~4, i=1~N) after the removal of the average of the magnetic signal waveforms $F_{ji}$ from the waveforms $F_{ji}$ (j=1~4, i=1~N) obtained by the gradiometers for detection are expressed as $f_i$ for simplicity and the magnetic signal waveforms $g_{ki}$ (k=1~2, i=1~N) after the removal of the average of the magnetic signal waveforms $G_{ki}$ from the waveforms $G_{ki}$ (k=1~2, i=1~N) are expressed as $g_i$ for simplicity. According to equation 11, a value of $\gamma$ is calculated by the method of least squares, giving a minimum evaluation function E (equation 10). FIGS. 4 and 5 describe the procedure for canceling external magnetic noise for each channel by using equation 11.

$$E=\Sigma(f_i-\gamma\times g_i)^2 \qquad \text{[Equation 10]}$$

$$\gamma=\Sigma(f_i\times g_i)/\Sigma(g_i)^2 \qquad \text{[Equation 11]}$$

The following explains detailed processing procedure with FIGS. 4 and 5. Here, $g_{1i}$ is the magnetic signal waveform detected by the gradiometer for compensation 10-a (with the baseline 11-a being 10 mm) with the baseline shorter than the 50-mm baselines 11-c of the gradiometers for detection and $g_{2i}$ is the magnetic signal waveform detected by the gradiometer for compensation 10-b (with the baseline 11-b being 30 mm). First, the magnetic signal waveform of external magnetic noise measured by the gradiometer for compensation 10-a having the shortest baseline is used to cancel the external magnetic noise primarily caused by variant noise cancellation rates.

Processing 15: uses equation 11 and calculates a value of $\gamma$ ($\gamma_1$, $\gamma_2$, $\gamma_3$, $\gamma_4$, and $\gamma_5$) for each gradiometer for detection 9 and the gradiometer for compensation 10-a. Calculations according to equations 12 through 16 give values of $\gamma_1$, $\gamma_2$, $\gamma_3$, $\gamma_4$, and $\gamma_5$.

Processing 16: can cancel the external magnetic noise primarily caused by variant noise cancellation rates for channels 1 to 4, giving magnetic signal waves $f'_{1i}$, $f'_{2i}$, $f'_{3i}$, $f'_{4i}$, and $g'_{2i}$. Calculations according to equations 17 through 21 give values of $f_{1i}$, $f_{2i}$, $f_{3i}$, $f_{4i}$, and $g'_{2i}$. It is considered that the external magnetic noise component due to different baselines of the two gradiometers for compensation remains in the $g'_{2i}$ magnetic signal waveform.

$$\gamma_1 = \Sigma(f_{1i} \times g_{1i})/\Sigma(g_{1i})^2 \qquad \text{[Equation 12]}$$

$$\gamma_2 = \Sigma(f_{2i} \times g_{1i})/\Sigma(g_{1i})^2 \qquad \text{[Equation 13]}$$

$$\gamma_3 = \Sigma(f_{3i} \times g_{1i})/\Sigma(g_{1i})^2 \qquad \text{[Equation 14]}$$

$$\gamma_4 = \Sigma(f_{4i} \times g_{1i})/\Sigma(g_{1i})^2 \qquad \text{[Equation 15]}$$

$$\gamma_5 = \Sigma(f_{2i} \times g_{1i})/\Sigma(g_{1i})^2 \qquad \text{[Equation 16]}$$

$$f'_{1i} = f_{1i} - \gamma_1 \times g_{1i} \qquad \text{[Equation 17]}$$

$$f'_{2i} = f_{2i} - \gamma_2 \times g_{1i} \qquad \text{[Equation 18]}$$

$$f'_{3i} = f_{3i} - \gamma_3 \times g_{1i} \qquad \text{[Equation 19]}$$

$$f'_{4i} = f_{4i} - \gamma_4 \times g_{1i} \qquad \text{[Equation 20]}$$

$$g'_{2i} = g_{2i} - \gamma_5 \times g_{1i} \qquad \text{[Equation 21]}$$

Then, computing proceeds to #1 (reference number 18) in FIG. 5 and executes processing 19 and 20 in the same manner as in processing 15.

Processing 19: calculates $\gamma_1$, $\gamma_2$, $\gamma_3$, and $\gamma_4$, according to equations 22 through 25.

Processing 20: cancels external magnetic noise from the magnetic signal waveforms $f'_{1i}$, $f'_{2i}$, $f'_{3i}$, and $f'_{4i}$ obtained from the execution of processing 16 by using the $g'_{2i}$ magnetic signal waveform as reference data and calculates $f''_{1i}$, $f''_{2i}$, $f''_{3i}$, and $f''_{4i}$, according to equations 26 through 29.

$$\gamma'_1 = \Sigma(f'_{1i} \times g'_{2i})/\Sigma(g'_{2i})^2 \qquad \text{[Equation 22]}$$

$$\gamma'_2 = \Sigma(f'_{2i} \times g'_{2i})/\Sigma(g'_{2i})^2 \qquad \text{[Equation 23]}$$

$$\gamma'_3 = \Sigma(f'_{3i} \times g'_{2i})/\Sigma(g'_{2i})^2 \qquad \text{[Equation 24]}$$

$$\gamma'_4 = \Sigma(f'_{4i} \times g'_{2i})/\Sigma(g'_{2i})^2 \qquad \text{[Equation 25]}$$

$$f''_{1i} = f'_{1i} - \gamma'_1 \times g'_{2i} \qquad \text{[Equation 26]}$$

$$f''_{2i} = f'_{2i} - \gamma'_2 \times g'_{2i} \qquad \text{[Equation 27]}$$

$$f''_{3i} = f'_{3i} - \gamma'_3 \times g'_{2i} \qquad \text{[Equation 28]}$$

$$f''_{4i} = f'_{4i} - \gamma'_4 \times g'_{2i} \qquad \text{[Equation 29]}$$

The method described above is the first method of external magnetic noise cancellation using a plurality of gradiometers for compensation with different baseline lengths, assuming that the magnetically shielded room in which the apparatus is placed has no frequency property.

Next, the following explains a second method of external magnetic noise cancellation for canceling the external magnetic noise that depends on the frequency property of the magnetically shielded room and is not canceled by the above first method of noise cancellation.

The magnetically shield room has a frequency property as a low-pass filter (LPF) with a cutoff frequency of 1 Hz or below. This low-pass filtering property behaves comparably to an RC circuit formed by resistors and capacitors. When external magnetic noise that can be defined by a step function enters the magnetically shielded room, a magnetic signal waveform $B_r$ as will be expressed by equation 30, where t is time and T is a time constant, is assumed to be observed in the room. To facilitate understanding, amplitude is set to 1 in equation 30 (supposing that external magnetic noise that can be expressed by a unit step function enters the magnetically shielded room).

$$B_r(t) = \exp(-t/T) \qquad \text{[Equation 30]}$$

From the expression for magnetic signal waveform $B_r(t)$, described by equation 30, magnetic signal waveform $B_1(t)$ of the magnetic field measured by the gradiometers for detection can be calculated by equation 31. Here, the time constants of the input coils and the compensating coils of the gradiometers for detection are respectively $T_1$ and $T_2$. Taylor expansion of equation 31 yields equation 32.

$$B_1(t) = \exp(-t/T_1) - \exp(-t/T_2) = \{1 - \exp(-t(1/T_2 - 1/T_1))\} \times \exp(-t/T_1) \qquad \text{[Equation 31]}$$

$$B_1(t) = (1/T_2 - 1/T_1) \times t \times \exp(-t/T_1) \qquad \text{[Equation 32]}$$

Similarly, assuming that the time constants of the input coils and the compensating coils of the gradiometers for compensation are respectively $T_3$ and $T_4$, magnetic signal waveform $B_2(t)$ measured by the gradiometers for compensation can be calculated by equation 33.

$$B_2(t) = (1/T_4 - 1/T_3) \times t \times \exp(-t/T_3) \qquad \text{[Equation 33]}$$

By using $\delta$ defined by equation 34, the magnetic signal waveform $B_2(t)$ of the external magnetic noise measured by the gradiometers for compensation is canceled from the magnetic signal waveform $B_1(t)$ measured by the gradiometers for detection. Then, magnetic signal waveform $(B_1 - \delta B_2)$ is obtained as will be described by equation 35. As in the case of equation 32, Taylor expansion of equation 35 yields equation 36.

$$\delta = (1/T_2 - 1/T_1)/(1/T_4 - 1/T_3) \qquad \text{[Equation 34]}$$

$$(B_1 - \delta B_2) = (1/T_4 - 1/T_3) \times \delta \times t \times \exp(-t/T_1) - \delta \times (1/T_4 - 1/T_3) \times t \times \exp(-t/T_3) =$$

$$(1/T_4 - 1/T_3) \times \delta \times t \times \{\exp(-(1/T_1 - 1/T_3) \times t) - 1\} \times \exp(-t/T_3) \qquad \text{[Equation 35]}$$

$$(B_1 - \delta B_2) = -(1/T_1 - 1/T_3) \times (1/T_4 - 1/T_3) \times \delta \times t^2 \times \exp(-t/T_3) \qquad \text{[Equation 36]}$$

If the time-independent terms of the amplitude expressions in equation 36 are substituted by $\eta$ (equation 37), equation 36 becomes a function as will be expressed by equation 38. As described above, equation 38 expresses the magnetic signal waveform obtained by canceling the external magnetic noise $B_2(t)$ from the detected waveform $B_1(t)$ using a fitting parameter $\delta$ determined by equation 34.

$$\eta = (1/T_1 - 1/T_3) \times (1/T_4 - 1/T_3) \times \delta \qquad \text{[Equation 37]}$$

$$(B_1 - \delta B_2) = -\eta \times t^2 \times \exp(-t/T_3) \qquad \text{[Equation 38]}$$

FIG. 6 shows samples of magnetic signal waveforms of external magnetic noise, calculated through theoretical calculation in Embodiment 1. In FIG. 6, the scales on the axis are for reading time (seconds) and the scales on the ordinate are for reading magnetic field strength derived from the function expressed by equation 30 with amplitude of 1.

Figure 6A:
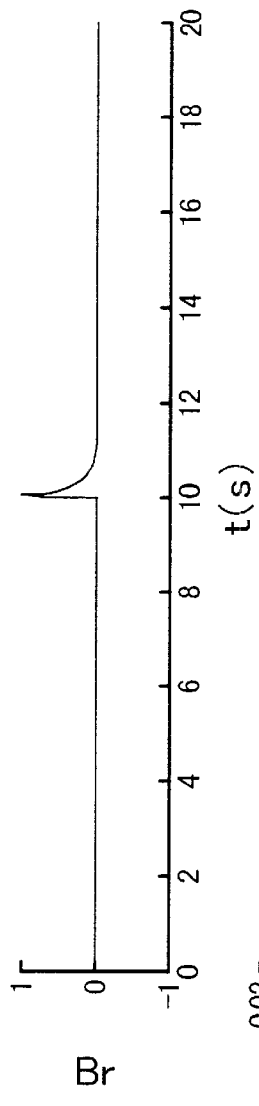
FIG. 6 shows samples of magnetic signal waveforms of external magnetic noise, calculated through theoretical calculation in Embodiment 1.
Figure 6B:
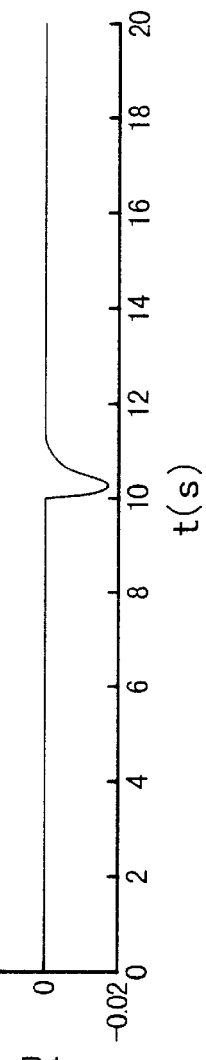
Figure 6C:
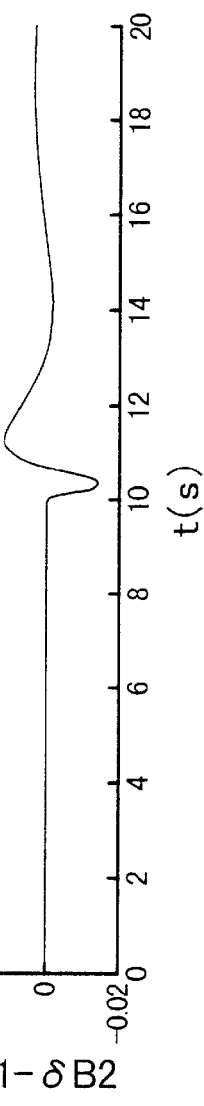

FIG. 6A shows the theoretically calculated magnetic signal waveform $B_r(t)$ (determined by equation 30) (corresponding to the magnetic signal waveform of external magnetic noise to be observed). FIG. 6B shows the magnetic signal waveform to be measured by the first-order SQUIOD gradiometers (gradiometers for detection). FIG. 6C shows the magnetic signal waveform $B_1(t)$ measured by the gradiometers for detection, from which external magnetic noise, or specifically, the magnetic signal waveform $B_2(t)$ measured by the gradiometers for compensation has been canceled, that is, the magnetic signal waveform $\{(B_1(t)-\delta B_2(t)\}$ obtained from equation 38.

Figure 6D:
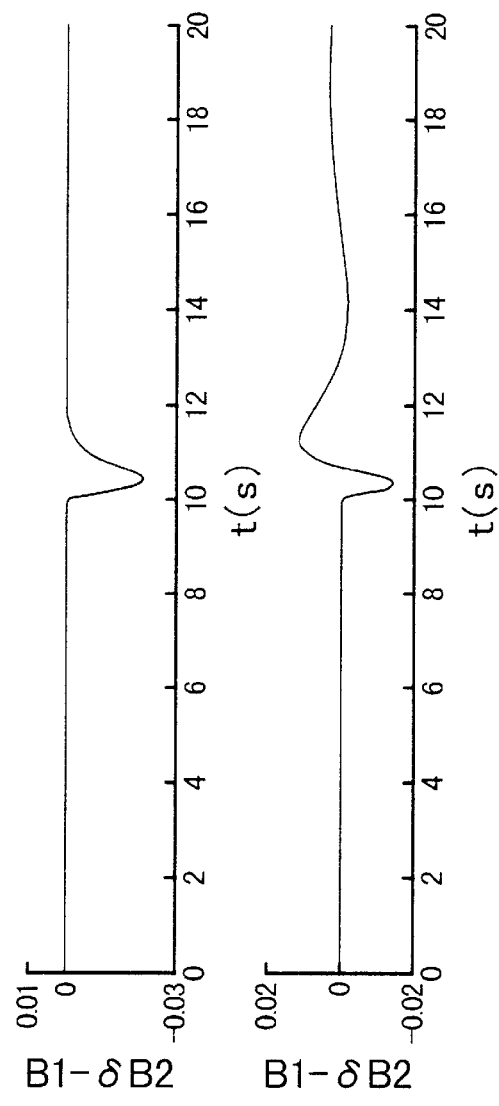

Actual measuring systems perform biomagnetic field measurement by using a high-pass filter (HPF). FIG. 6D shows the magnetic signal waveform after being manipulated to pass through a second-order Butterworth-type high-pass filter of 0.1 Hz for the purpose of simulating an actually measured magnetic signal waveform, where the waveform is the one has been measured by the gradiometers for detection, from which external magnetic noise, or specifically, the magnetic signal waveform measured by the gradiometers for compensation has been canceled, that is, the magnetic signal waveform $\{(B_1(t)-\delta B_2(t)\}$ obtained from equation 38.

In the above calculations, it has been assumed that the time constant for $B_r$ is T=0.2 seconds, the time constants for $B_1$ are $T_1$=0.2 seconds and $T_2$=0.21 seconds, the time constant for $(B_1-\delta B_2)$ is $T_3$=0.2 seconds. FIG. 6A shows the magnetic signal waveform of external magnetic noise to be observed, which has been calculated through simulation of the noise supposed to have occurred at the time reading of 10 seconds, characterized by a step function.

The waveforms $B_r(t)$ and $B_1(t)$ well resemble the corresponding magnetic signal waveforms that have been actually measured by Brake et al. at the University of Twente (Meas. Sci. Technol., Vol. 2, pp. 596–601 [1991]).

Figure 7:
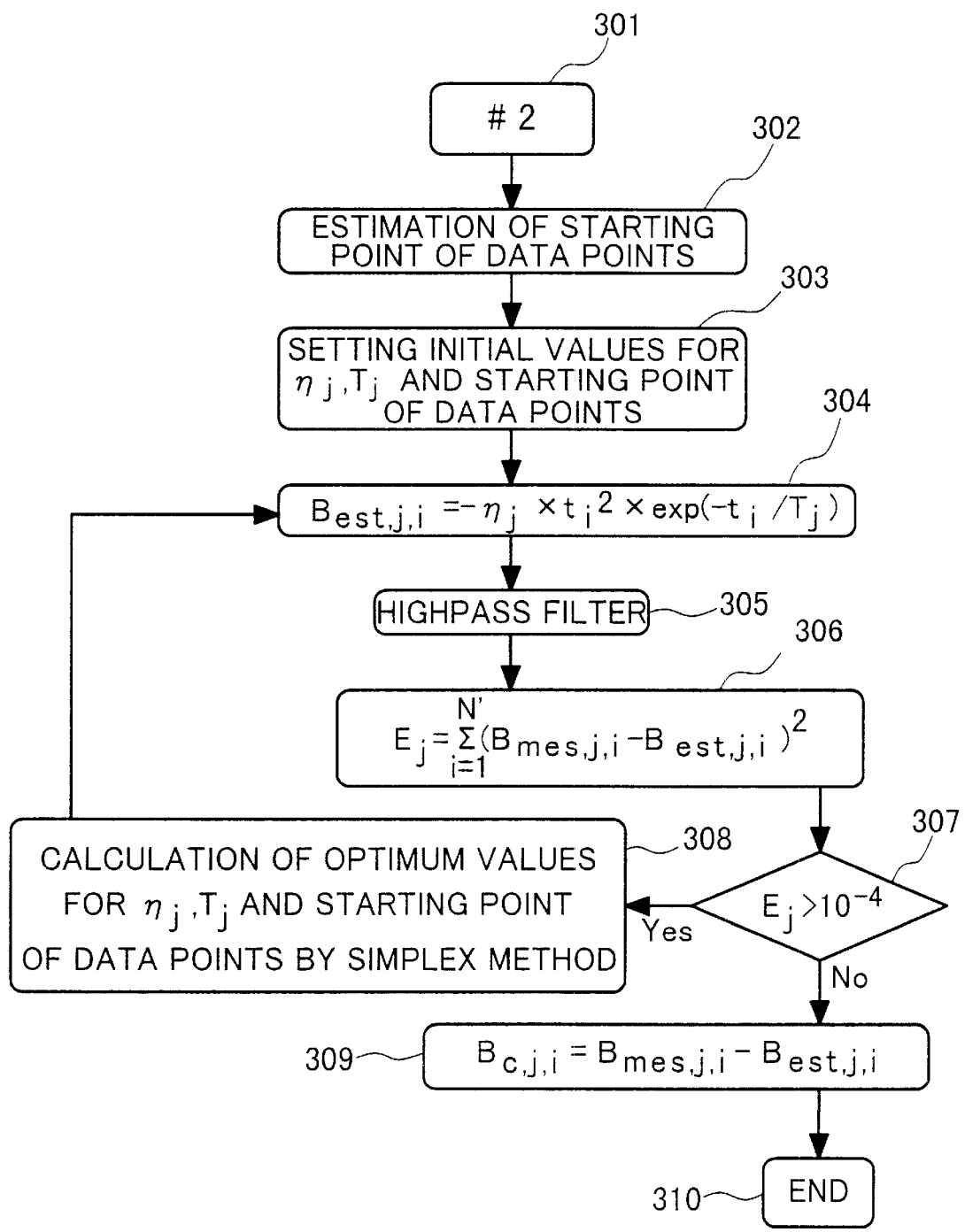
FIG. 7 is a flowchart for explaining the method of canceling the external magnetic noise due to the frequency property of the magnetically shielded room in Embodiment 1.

FIG. 7 is a flowchart for explaining the method of canceling the external magnetic noise due to the frequency property of the magnetically shielded room in Embodiment 1 (a second method of canceling external magnetic noise). Using FIG. 7, the second method of external magnetic noise cancellation will be explained below. Initially, the processing according to the first method of external magnetic noise cancellation is executed as shown in FIGS. 4 and 5. Then, distorted magnetic signal waveform portions due to the frequency property of the magnetically shielded room are canceled, according to equation 38. For all channels j (j=1~4), each of the following processing 302 to 309 is executed sequentially.

Processing 302: finds an initial data point at which distortion first appears in the magnetic signal waveform (initial point of external magnetic noise generation) (corresponding to the spike appearing at 10 seconds on the axis in FIG. 6). Processing 302 calculates a second-order gradient waveform of the measured waveform (first waveform before canceling external magnetic noise) in terms of time, detects a peak, and interprets the time at which the peak appears as an initial data point (initial point). The initial point may be known by reading the peak of a magnetic signal waveform displayed on the screen of a display device or using the magnetic signal waveform measure by a flux-gate magnetometer installed outside the magnetically shielded room.

Processing 303: sets amplitude $\eta_j$ and a time constant $T_j$ for channels j (j=1~4) ($T_j$ is $T_3$ (equation 38) of channels j) as initial values at the initial point (initial data point at which the distortion of the waveform first occurs). For example, the processing sets $\eta_j$ at 1 and $T_j$ at 0.2 seconds.

Processing 304: calculates magnetic signal waveform $B_{est, j, i}$ through theoretical calculation according to equation 39 for all channels j (j=1~4).

Processing 305: executes high-pass filtering.

Processing 306: calculates evaluation function $E_j$ by calculating the sum of least squares of measurements $B_{mes, j, i}$ and $B_{est, j, i}$, according to equation 40. In equation 40, addition symbol $\Sigma$ indicates addition for i=1~i=N' (N' indicates the number of sampling points $t_i$ along the time axis for the waveform of the measurement $B_{mes, j, i}$).

$$B_{est, j, i} = -\eta \times t_i^2 \times \exp(-t_{i/Tj}) \qquad \text{[Equation 39]}$$

$$E_j = \Sigma(B_{mes, j, i} - B_{est, j, i})^2 \qquad \text{[Equation 40]}$$

Processing 307: executes processing 308 if $E_j$ is greater than a preset reference value (for example, $E_j > 10^{-4}$) or processing 309 if $E_j$ is equal to or less than the preset reference value (for example, $E_j \leq 10^{-4}$).

Processing 308: sets again amplitude $\eta_j$, a time constant $T_j$, and an initial data point (initial point) by a simplex method to set a smaller value of evaluation function $E_j$ and re-executes processing 304.

Processing 309: theoretically calculates magnetic signal waveform $B_{est, j, i}$ by using the amplitude $\eta_j$, time constant $T_j$, and initial data point (initial point) that have been set as optimum solutions, according to equation 39, and subtracts the waveform $B_{est, j, i}$ from the waveform $B_{mes, j, i}$ obtained through the first method of external magnetic noise cancellation, according to equation 41. As a result, waveform $B_{c, j, i}$ for channels j (j=1~4) is obtained from which external magnetic noise has been canceled by the second method of external magnetic noise cancellation.

$$B_{c, j, i} = B_{mes, j, i} - B_{est, j, i} \qquad \text{[Equation 41]}$$

The method explained above is the second method of external magnetic noise cancellation for canceling the external magnetic noise occurring dependent on the frequency property of the magnetically shielded room, still remaining after the first external magnetic noise cancellation method is executed.

Embodiment 2

Next, the results of executing the above procedures for the data from the measurement performed by using the SQUID gradiometers arranged as shown in FIGS. 1 and 2 will be explained below. In and outside the magnetically shielded, the initial waveform of external magnetic noise was recorded at the same time.

Figure 8:
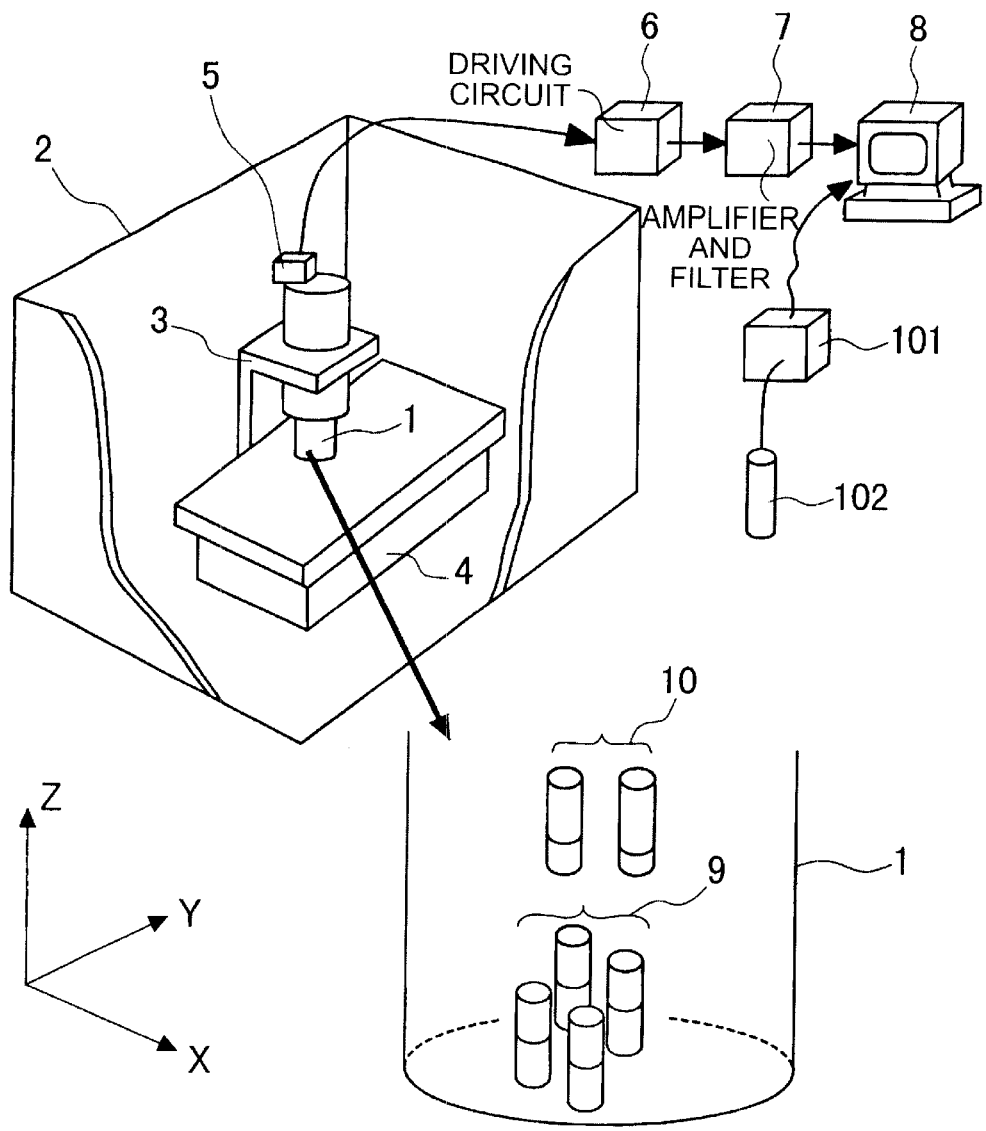
FIG. 8 is a schematic illustration showing an example of the configuration of a magnetic field measuring apparatus according to a preferred Embodiment 2 of the present invention.

FIG. 8 is a schematic illustration showing an example of the configuration of a magnetic field measuring apparatus according to a preferred Embodiment 2 of the present invention. A sensor part of flux-gate type magnetometer 102 is placed outside the magnetically shielded room about five meters apart from the room to detect a magnetic field in the same z direction as the direction in which the firs-order SQUID gradiometers installed in the room detect a magnetic field. The sensor part 102 of flux-gate type magnetometer 102 operates with the main body of flux-gate magnetometer 101 as a magnetometer. The output from the main body 101 is delivered to the computer 8 through only a low-pass filter having a corner frequency of 100 Hz. The first-order SQUID gradiometers are arranged as shown in FIGS. 1 and 2. The outputs from the SQUID gradiometers are delivered to the computer through a band-pass filter of 0.1 Hz to 100 Hz and a notch filter of 50 Hz.

FIG. 9 shows a sample magnetic signal waveform measured by the flux-gate magnetometer included in the magnetic field measuring apparatus of Embodiment 2. In FIG. 9, the scales on the axis are for reading time (minutes) and the scales on the ordinate are for reading magnetic field strength (unit: microtesla ($\mu$T)). In the sample waveform shown in FIG. 8, strong magnetic spikes of 1.2 $\mu$T or more appear at intervals of about 10 minutes. These spikes are due to the magnetic field generated by a train that runs at intervals of about 10 minutes, about 50 meters apart from the magnetically shielded room.

FIG. 10 shows samples of magnetic signal waveforms measured by the flux-gate magnetometer and the SQUID gradiometers included in the magnetic field measuring apparatus of Embodiment 2. In FIG. 10, the scales on the axis are for reading time (seconds) and the scales on the ordinate are for reading magnetic field strength (unit: picotesla (pT) for FIGS. 10-A, B, C, D, and microtesla ($\mu$T) for FIG. 10E). The magnetic signal waveforms shown in FIG. 10 have been recorded by the measurement during a period marked 201 in FIG. 9 and are those detected by the gradiometers for detection and the one measured by the flux-gate magnetometer (an enlarged view of the section of the waveform during a period 201 shown in FIG. 9). Magnetic field measurement was performed with no object to be inspected being on the bed.

FIGS. 10A, 10B, 10C, and 10D show the waveforms measured by the first-order SQUID gradiometers in the magnetically shielded room, corresponding to the $f_{1i}$, $f_{2i}$, $f_{3i}$, and $f_{4i}$ outputs of the gradiometers for detection (FIG. 2), 9-$a$ (ch. 1), 9-$b$ (ch. 2), 9-$c$ (ch. 3), and 9-$d$ (ch. 4), where ch. i means channel i.

Figure 10A:
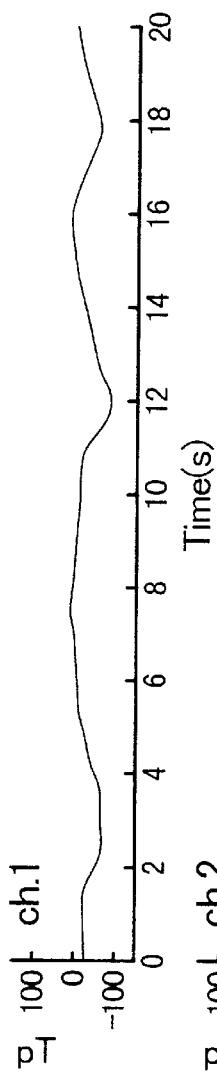
FIG. 10 shows samples of magnetic signal waveforms measured by the flux-gate magnetometer and the SQUID gradiometers included in the magnetic field measuring apparatus of Embodiment 2.
Figure 10B:
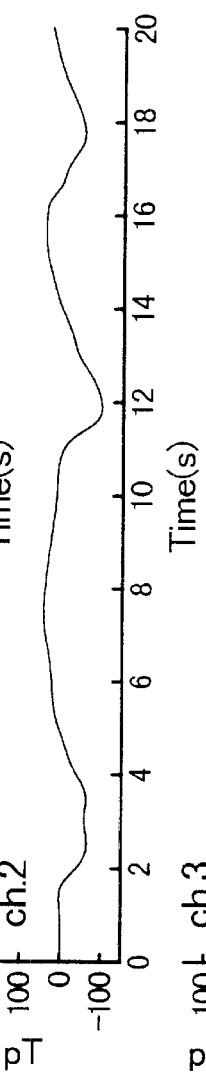
Figure 10C:
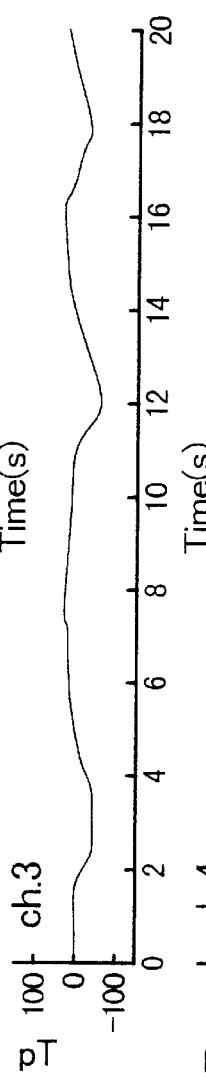
Figure 10D:
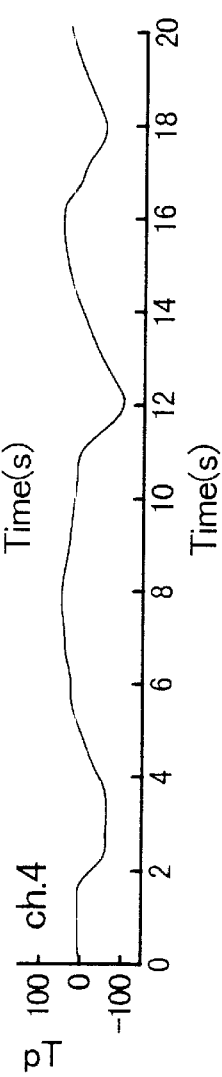
Figure 10E:
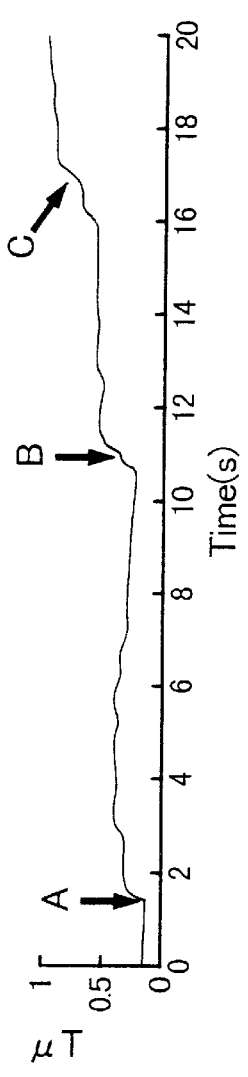

FIG. 10E shows the waveform measured by the flux-gate magnetometer outside the magnetically shielded room. FIG. 10E indicates that environmental noise characteristic of step function occurs at times A, B, and C. When viewing the waveforms for ch. 1 through ch. 4 shown in FIGS. 10A through 10D, it is seen that external magnetic noise also occurs in the magnetically shielded room at times A and B that are regarded as initial points. By comparison in view of strength for the waveforms of the external magnetic noise for ch. 1 through 4, it is seen that the amplitude of the noise varies among the channels.

As indicated by the magnetic signal waveforms for ch. 1 to ch. 4, even if the gradiometers of equal-length baseline for detection are used for measurement, the amplitude of the measured external magnetic noise varies among them. This is mainly because that the channels have variant noise cancellation rates, which is concluded through consideration of equation 5.

The input coils and compensating coils of the gradiometers for detection and the gradiometers for compensation shown in FIGS. 1, 2, and 8 are made by winding superconductive wires by hand. Their noise cancellation rates fall in a range of about $10^{-2}$ to $10^{-3}$ (40 dB to 60 dB) Small difference in the noise cancellation rates is significantly reflected in the measured magnetic signal waveforms. This problem of variant noise cancellation rates of channels is inevitable for manually-made coils. If the noise cancellation rates are adjusted to a certain rate, it is necessary to make an adjustment of the coils placed in a superconductive state in a uniform magnetic field of $10^{-3}$ or below. In actuality, the adjustment work like this is very difficult.

When an uneven strong noise magnetic field exists, the outputs from the gradiometers considerably vary in amplitude because of variant noise cancellation rates of the channels. Precise cancellation of such external magnetic noise is difficult by using a specific channel as a reference channel for inferring the noise and subtracting the reference channel output signal used for this purpose from each channel output signal. Therefore, for a multi-channel magnetic field measuring apparatus, it is necessary to determine what amount of external magnetic noise to be canceled for each channel.

Figures 11A, 11B, 11C, 11D, 11E, 11F:
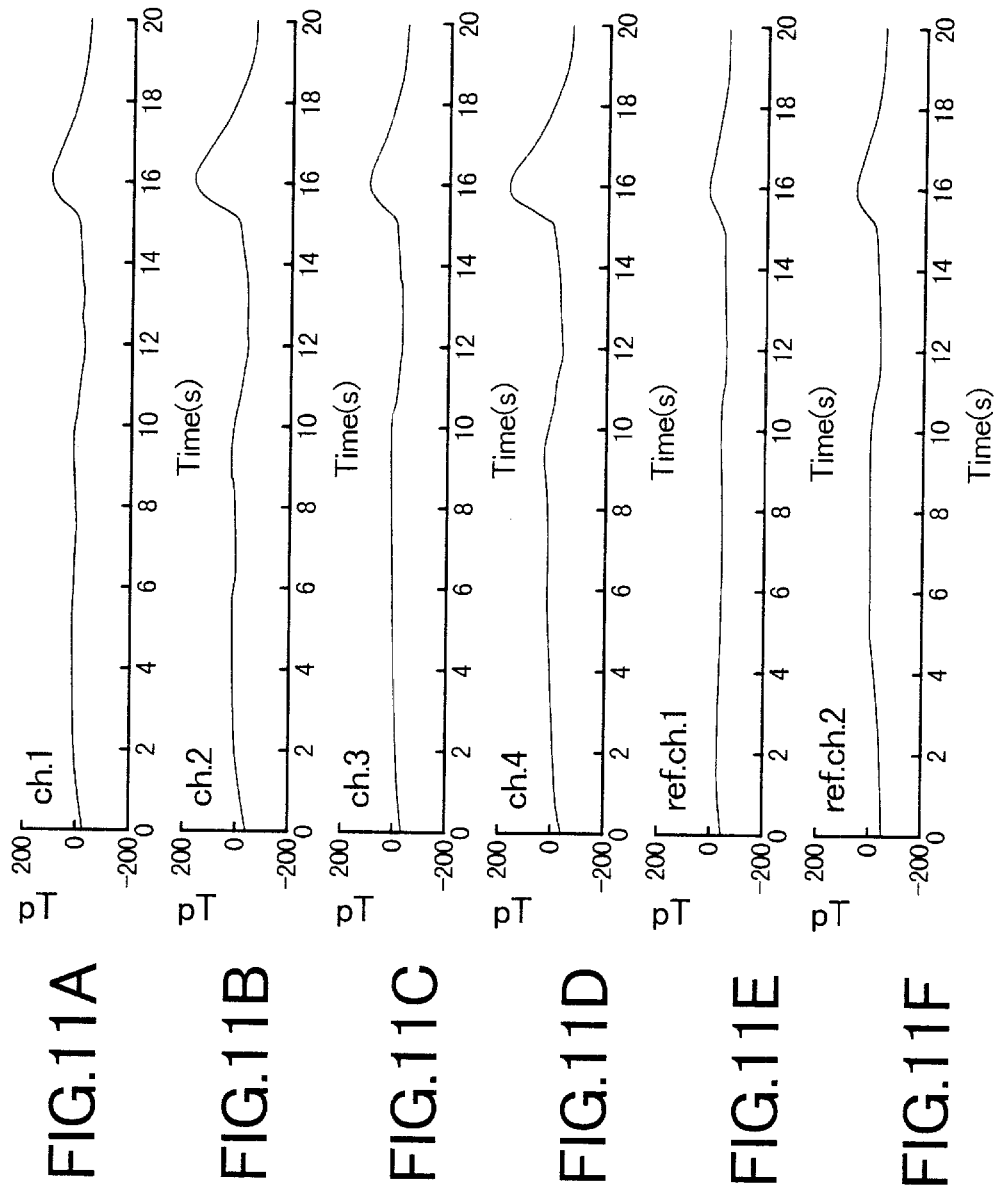
FIG. 11 shows samples of magnetic signal waveforms measured by the SQUID gradiometers included in the magnetic field measuring apparatus of Embodiment 2 with no object to be inspected.
Figure 13A:
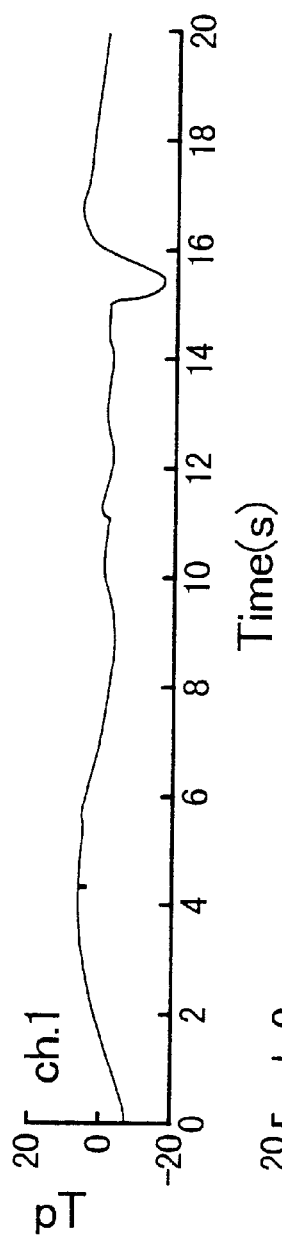
FIG. 13 shows samples of magnetic signal waveforms after external magnetic noise is further canceled from the magnetic signal waveforms shown in FIG. 12 by using the second gradiometer for compensation included in Embodiment 1 (according to the procedure shown in FIG. 5)
Figure 13B:
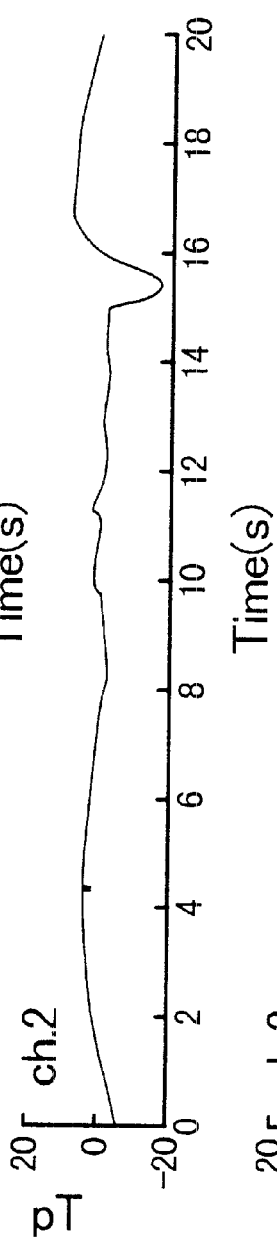
Figure 13C:
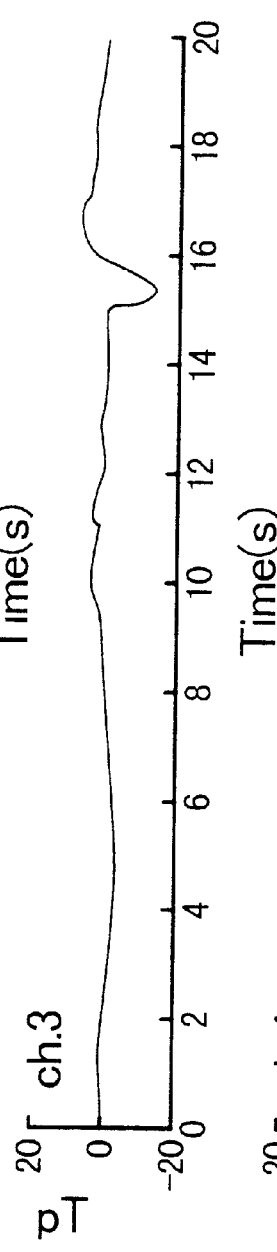
Figure 13D:
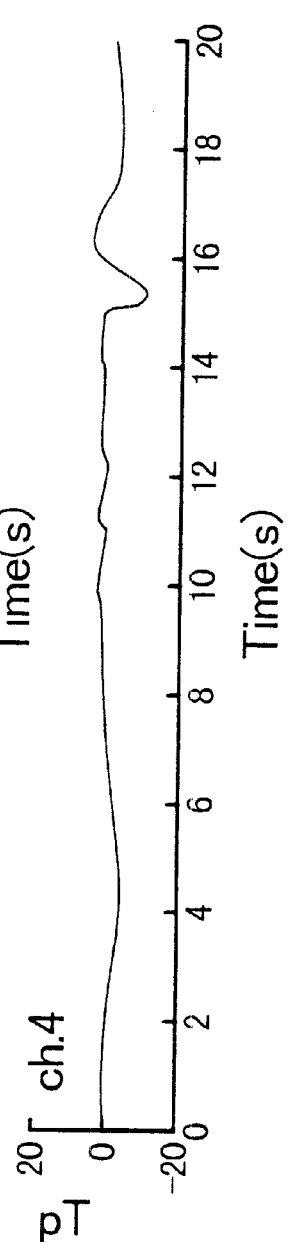
Figure 16A:
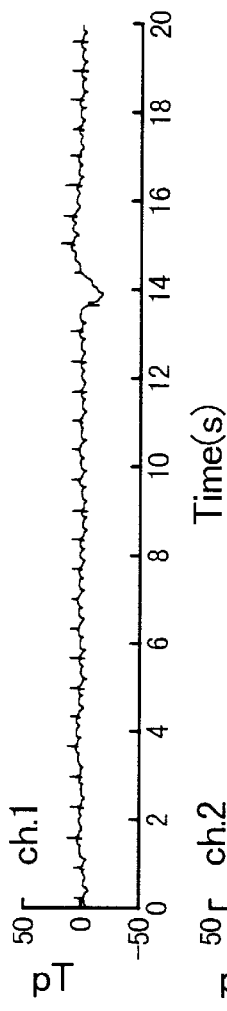
FIG. 16 shows samples of magnetic signal waveforms after external magnetic noise is canceled from the waveforms shown in FIG. 15 by using the first gradiometer for compensation included in Embodiment 1 (according to the procedure shown in FIG. 4)
Figure 16B:
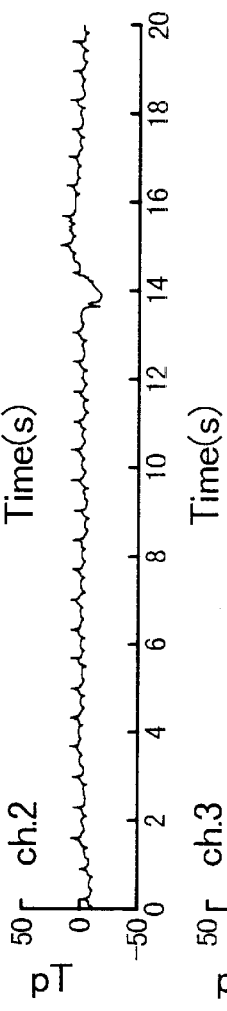
Figure 16C:
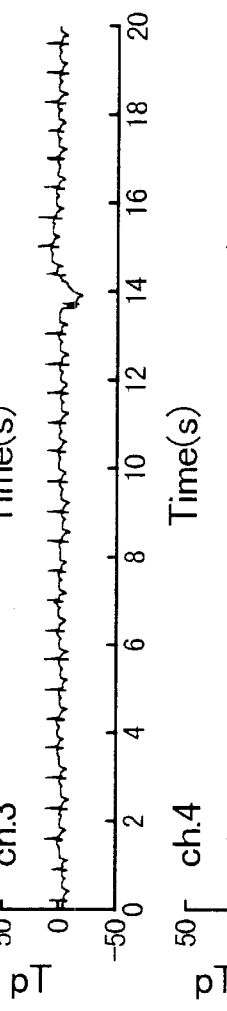
Figure 16D:
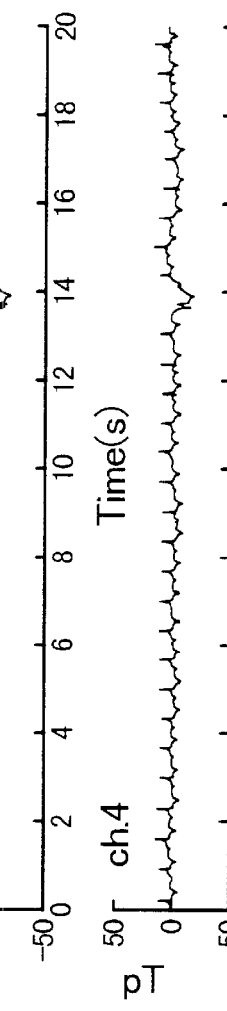
Figure 16E:
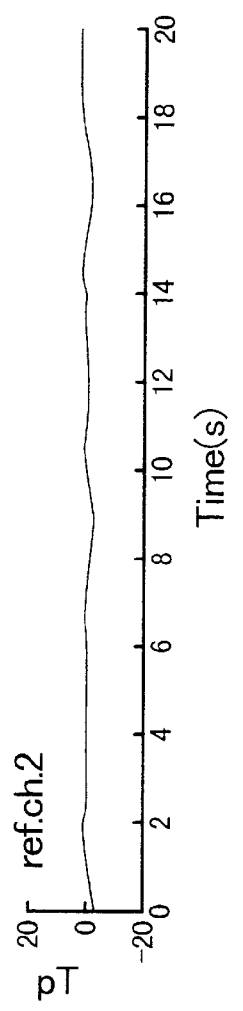

FIG. 11 shows samples of magnetic signal waveforms measured by the SQUID gradiometers included in the magnetic field measuring apparatus of Embodiment 2 with no object to be inspected being on the bed in a time zone different from the time zone for sampling the samples shown in FIG. 10. In FIG. 11, the scales on the axis are for reading time (seconds) and the scales on the ordinate are for reading magnetic field strength (unit: pT). FIGS. 11A, 11B, 11C, and 11D corresponds to the magnetic signal waveforms $f_{1i}$, $f_{2i}$, $f_{3i}$, and $f_{4i}$ measured by the gradiometers for detection 9-$a$ (ch. 1), 9-$b$ (ch. 2), 9-$c$ (ch. 3), and 9-$d$ (ch. 4) shown in FIGS. 1, 2, and 8. FIGS. 11E and 11F correspond to the magnetic signal waveforms $g_{1i}$ and $g_{2i}$ measured by the gradiometers for compensation 10-$a$ (ref. ch. 1) and 10-$b$ (ref. c. 2).

In the waveform $g_{1i}$ of ref. ch. 1 (FIG. 11E) and the waveform $g_{2i}$ of ref. ch. 2 (FIG. 11F), the occurrence of strong external magnetic noise of the order of 100 pT is observed around the time reading of 16 seconds. Although the amplitude of the waveform $g_{1i}$ (FIG. 11E) measured by the gradiometer for compensation (ref. ch. 1) having a baseline of 10 mm is the smallest, the same rise of waveform of external magnetic noise as in the waveforms $f_{1i}$, $f_{2i}$, $f_{3i}$, and $f_{4i}$ shown in FIGS. 11A (ch. 1) to 11D (ch. 4) also appears in the waveform shown in FIG. 11E.

FIG. 12 shows samples of magnetic signal waveforms after external magnetic noise is canceled from the magnetic signal waveforms shown in FIG. 11 by using the first gradiometer for compensation included in Embodiment 1 (according to the procedure shown in FIG. 4). In FIG. 12, the scales on the axis are for reading time (seconds) and the scales on the ordinate are for reading magnetic field strength (unit: pT). The waveforms shown in FIG. 12 are the results of the execution of processing 15 and 16 shown in FIG. 4 by using the magnetic signal waveform $g_{1i}$ of ref. ch1 shown in FIG. 11 and through calculation according to equations 12 through 21. Specifically, FIGS. 12A, 12B, 12C, 12D, and 12E correspond to $f'_{1i}$, $f'_{2i}$, $f'_{3i}$, $f'_{4i}$, and $g'_{2i}$ which are the results of calculating equations 17, 18, 19, 20, and 21, respectively.

In the magnetic signal waveforms shown in FIGS. 12A, 12B, 12C, and 12D, the amplitude of external magnetic noise is reduced about one-fourth of the noise in the corresponding waveforms shown in FIGS. 11A, 11B, 11C, and 11D, but significant external magnetic noise still remains.

FIG. 13 shows samples of magnetic signal waveforms after external magnetic noise is further canceled from the magnetic signal waveforms shown in FIG. 12 by using the second gradiometer for compensation included in Embodiment 1 (according to the procedure shown in FIG. 5). In FIG. 13, the scales on the axis are for reading time (seconds) and the scales on the ordinate are for reading magnetic field strength (unit: pT). The waveforms shown in FIG. 13 are the results of the execution of further processing 19 and 20 shown in FIG. 5 by using the magnetic signal waveform $g'_{2i}$ of ref. ch2 shown in FIG. 12. Specifically, FIGS. 13A, 13B, 13C, and 13D correspond to $f''_{1i}$, $f''_{2i}$, $f''_{3i}$, and $f''_{4i}$, which are the results of calculating equations 26, 27, 28, and 29, respectively.

In the resulting waveforms shown in FIG. 13, significant external magnetic noise is almost canceled, but remaining noise of the order of 20 pT appears near the time reading of 15 seconds. The waveforms of remaining noise in FIGS. 13A, 13B, 13C, and 13D are similar to the magnetic signal waveform obtained by simulation shown in FIG. 6D. The remaining noise signal waveforms shown in FIG. 13 are considered to have occurred due to that the low-pass filter property of the magnetically shielded room distorts the signals of environmental noise characteristic of step function mixed in the measured magnetic field, as explained above for FIG. 6.

These remaining noise signal waveforms, as evident from equation 38, depend on the time constant $T_3$ of the input coils of the gradiometers for compensation, and differ position by position in which the gradiometers for detection are placed, or in other words, per channel number of each gradiometer for detection, as seen from the results shown in FIG. 13.

Therefore, this means that the noise signal waveform that remains after the execution of the procedure for canceling external magnetic noise by using the first and second gradiometers for compensation included in Embodiment 1 varies, depending on the positional relation between the gradiometers for detection and the gradiometers for compensation. To cancel the remaining external magnetic noise shown in FIG. 13, the steps of processing 302 to 309 shown in FIG. 7 are executed.

FIG. 14 shows samples of magnetic signal waveforms after the external magnetic noise occurring due to the frequency property of the magnetically shielded room is canceled from the magnetic signal waveforms shown in FIG. 13 (according to the procedure shown in FIG. 7). In FIG. 14, the scales on the axis are for reading time (seconds) and the scales on the ordinate are for reading magnetic field strength (unit: pT). The waveforms shown in FIGS. 14A, 14B, 14C, and 14D correspond to the results of calculation according to equations 39 to 41 for the waveforms shown in FIGS. 13A, 13B, 13C, and 13D, respectively.

As apparent from FIGS. 14A, 14B, 14C, and 14D, external magnetic noise is almost canceled, but a spiky peak of remaining noise appears near the time reading of 15 seconds, which is regarded as the initial point at which the environmental noise characteristic of step function has mixed into the measured magnetic field, for the waveforms of the channels ch. 1 to ch. 4. This last remaining environmental noise showing a spiky peak is considered to have occurred due to variant time constants $T_1$ of the input coils of the gradiometers for detection.

FIG. 15 show s samples of magnetic signal waveforms measured by the SQUID gradiometers of the magnetic field measuring apparatus of Embodiment 2 during the measurement of a magnetic field originating from the object to be inspected that is a heart. In FIG. 15, the scales on the axis are for reading time (seconds) and the scales on the ordinate are for reading magnetic field strength (unit: pT). In the samples shown in FIG. 15, the occurrence of external magnetic noise is observed near the time reading of 14 seconds. The magnetic signal waveforms shown in FIGS. 15A, 15B, 15C, 15D, 15E, and 15F are respectively similar to the waveforms of shown in FIGS. 11A, 11B, 11C, 11D, 11E, and 11F.

FIG. 16 shows samples of magnetic signal waveforms after external magnetic noise is canceled from the waveforms shown in FIG. 15 by using the first gradiometer for compensation included in Embodiment 1 (according to the procedure shown in FIG. 4). In FIG. 16, the scales on the axis are for reading time (seconds) and the scales on the ordinate are for reading magnetic field strength (unit: pT). Like FIGS. 12A, 12B, 12C, 12D, and 12E, FIGS. 16A, 16B, 16C, 16D, and 16E show the results of execution of processing 15 and 16 by using the magnetic signal waveform (FIG. 15E) of ref. ch. 1 shown in FIG. 15. In the samples shown in FIG. 16, significant external magnetic noise is almost canceled only by executing the procedure shown in FIG. 4, but remaining noise of the order of 20 pT appears near the time reading of 14 seconds.

FIG. 17 shows samples of magnetic signal waveforms after external magnetic noise is canceled from the waveforms shown in FIG. 16 by using the second gradiometer for compensation included in Embodiment 1 (according to the procedure shown in FIG. 5). In FIG. 17, the scales on the axis are for reading time (seconds) and the scales on the ordinate are for reading magnetic field strength (unit: pT) Like FIGS. 13A, 13B, 13C, and 13D, FIGS. 17A, 17B, 17C, and 17D show the results of execution of processing 19 and 20 by using the magnetic signal waveform (FIG. 16E) of ref. ch. 2 shown in FIG. 16. As in FIGS. 13A, 13B, 13C, and 13D, the magnetic signal waveforms shown in FIGS. 17A, 17B, 17C, and 17D are similar to the magnetic signal waveform obtained by simulation shown in FIG. 6D, but external magnetic noise still remains as shown.

FIG. 18 shows samples of magnetic signal waveforms after the external magnetic noise occurring due to the frequency property of the magnetically shielded room is canceled from the magnetic signal waveforms shown in FIG. 17 (according to the procedure shown in FIG. 7). In FIG. 18, the scales on the axis are for reading time (seconds) and the scales on the ordinate are for reading magnetic field strength (unit: pT). Like FIGS. 14A, 14B, 14C, 14D, FIGS. 18A, 18B, 18C, and 18D, show the results of execution of the steps of processing 302 to 309 shown in FIG. 7 to cancel the external magnetic noise remaining in the waveforms shown in FIGS. 17A, 17B, 17C, and 17D.

As apparent from the results shown in FIG. 18, external magnetic noise is almost canceled and the magnetic field originating from the heart, the object to be inspected, is clearly detected, but a spiky peak of environmental noise remains uncanceled and appears at the time reading about 13.8 seconds, which is the same as for the results shown in FIG. 14.

As regards the results shown in FIG. 16, because significant external magnetic noise is almost canceled only be executing the procedure shown in FIG. 4, the procedure (FIG. 7) for canceling the external magnetic noise due to the frequency property of the magnetically shielded room may be executed to cancel the remaining external magnetic noise of the order of 20 pt appearing near the time reading of 14 seconds in the waveforms shown in FIGS. 16A, 16B, 16C, and 16D, then the same result can be gained.

In other words, depending on the judgment of the result of canceling external magnetic noise by using the first gradiometer for compensation (FIG. 4), determination may be made as to whether to directly execute the procedure (FIG. 7) for canceling the external magnetic noise due to the frequency property of the magnetically shielded room. After this determination, if it is not necessary to execute the procedure for canceling external magnetic noise by using the second gradiometer for compensation shown in FIG. 5, faster operation of canceling most of external magnetic noise can be performed.

FIG. 22 shows a list of the time constants for data1 and data2 ($T_3$ in equation 38 (units: seconds)) obtained from the respective waveforms shown in FIGS. 13 and 17 in Embodiment 2. The list of FIG. 22 contains the time constants inferred by using equation 38 to cancel the remaining external magnetic noise in FIGS. 13 and 17. According to the list of FIG. 22, it is seen that the time constants $T_3$ slightly differ which have been inferred from the magnetic signal waveforms measured by the gradiometers for detection 9-*a* (ch. 1), 9-*b* (ch. 2), 9-*c* (ch 3), and 9-*d* (ch. 4) arranged as shown in FIGS. 1, 2, and 8.

FIG. 22 implies that how much the time constant $T_3$ of the input coils of the gradiometers for compensation influences the gradiometers for detection differs per gradiometer for detection and the influence of time constant $T_3$ differs, depending on the position of each gradiometer for detection. To evaluate the difference among the time constants, subtraction is executed for the channels' waveforms shown in FIGS. 13 and 17.

FIG. 19 shows samples of magnetic signal waveforms after inter-channel differential processing is applied to the waveforms shown in FIGS. 13A, 13B, 13C, and 13D. In FIG. 19, the scales on the axis are for reading time (seconds) and the scales on the ordinate are for reading magnetic field strength (unit: pT). FIGS. 19A, 19B, and 19C show the results of subtracting the waveform of channel 1 from the waveform of channel 2, the waveform of channel 3, and the waveform of channel 4, multiplied by (−1), respectively.

Similarly, FIG. 20 shows samples of magnetic signal waveforms after inter-channel differential processing is applied to the waveforms shown in FIGS. 17A, 17B, 17C, and 17D. In FIG. 20, the scales on the axis are for reading time (seconds) and the scales on the ordinate are for reading magnetic field strength (unit: pT). FIGS. 20A, 20B, and 20C show the results of subtracting the waveform of channel 1 from the waveform of channel 2, the waveform of channel 3, and the waveform of channel 4, multiplied by (−1), respectively.

In the samples shown in FIGS. 19 and 20, remaining external magnetic noise appears in the magnetic signal waveforms (difference) shown in FIGS. 19C and 20C, which are obtained by subtracting the waveform of channel 1 from the waveform of channel 4. There is the greatest difference between the time constants $T_3$ of these channels. The above result indicates that how much the time constant (time constant $T_3$ inferred by using equation 38) influences the measurement differs, depending on the position of each gradiometer for detection. In other words, the values of time constant $T_3$ are distributed spatially.

Figures 21A, 21B, 21C, 21D:
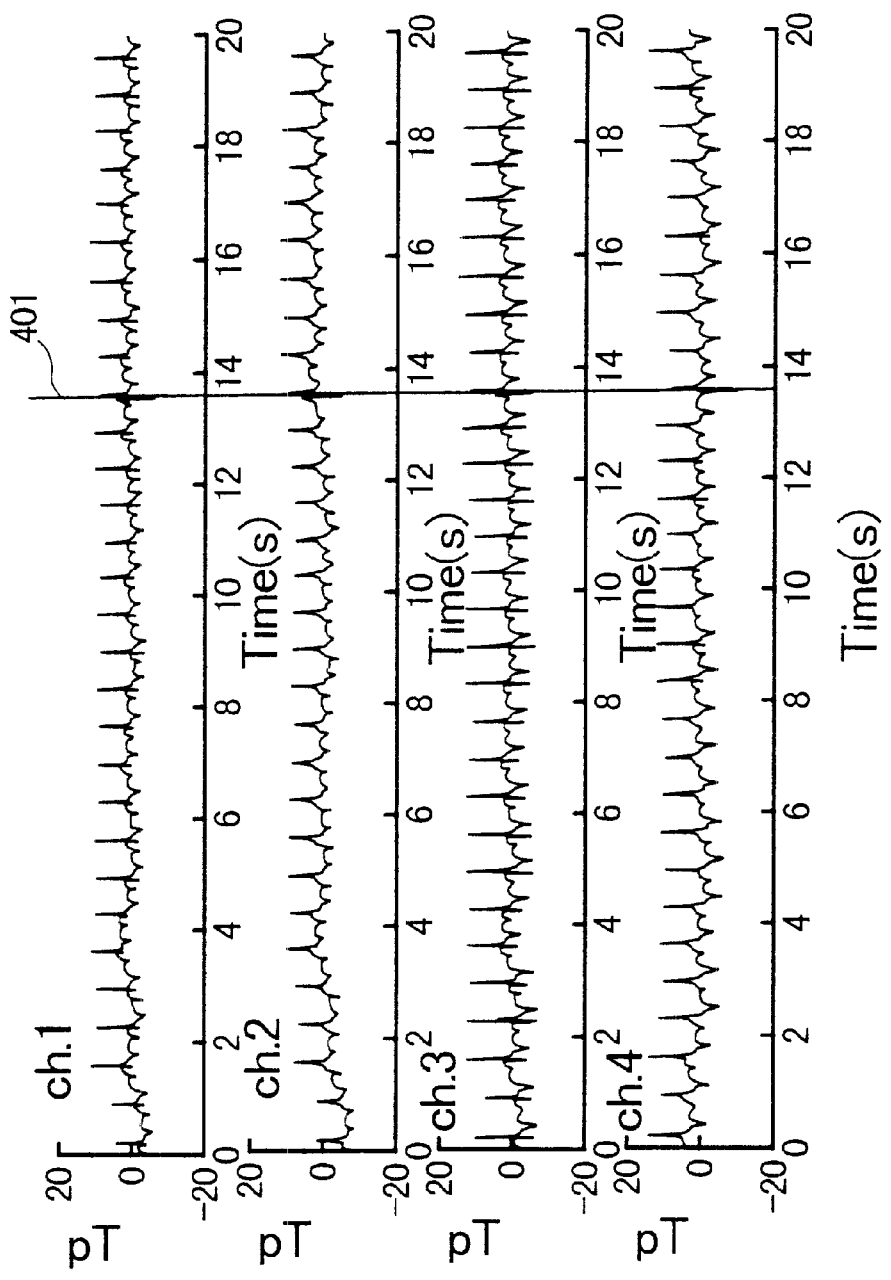
FIG. 21 shows examples of displaying magnetic signal waveforms from which external magnetic noise has been canceled in Embodiment 2.

FIG. 21 shows examples of displaying magnetic signal waveforms from which external magnetic noise has been canceled in Embodiment 2. These examples of display allow the person who conducts the measurement to easily understand the magnetic signal waveform remaining after external magnetic noise cancellation. In FIG. 21, the scales on the axis are for reading time (seconds) and the scales on the ordinate are for reading magnetic field strength (unit: pT) FIGS. 21A, 21B, 21C, and 21D correspond to FIGS. 18A, 18B, 18C, and 18D. At the time reading corresponding to the initial point at which external magnetic noise begins to occur, a straight line 401, alternatively, a dot, a color dot, a dotted line, a color line, a bold line, etc., is shown together with the display of a magnetic signal waveform from which external magnetic noise has been canceled on the screen of a display device. In this way, the apparatus configured in Embodiment 2 allows the user to notice that there is a possibility of being affected by external magnetic noise around the initial point.

A time value obtained by processing 303 shown in FIG. 7 is used as the time reading at which the straight line 401 is displayed. Alternatively, the time reading at which the straight line 101 is displayed may be detected from a time-differential waveform of a magnetic signal waveform measured by the flux-gate magnetometer shown in FIG. 8.

Embodiment 3

Figure 23:
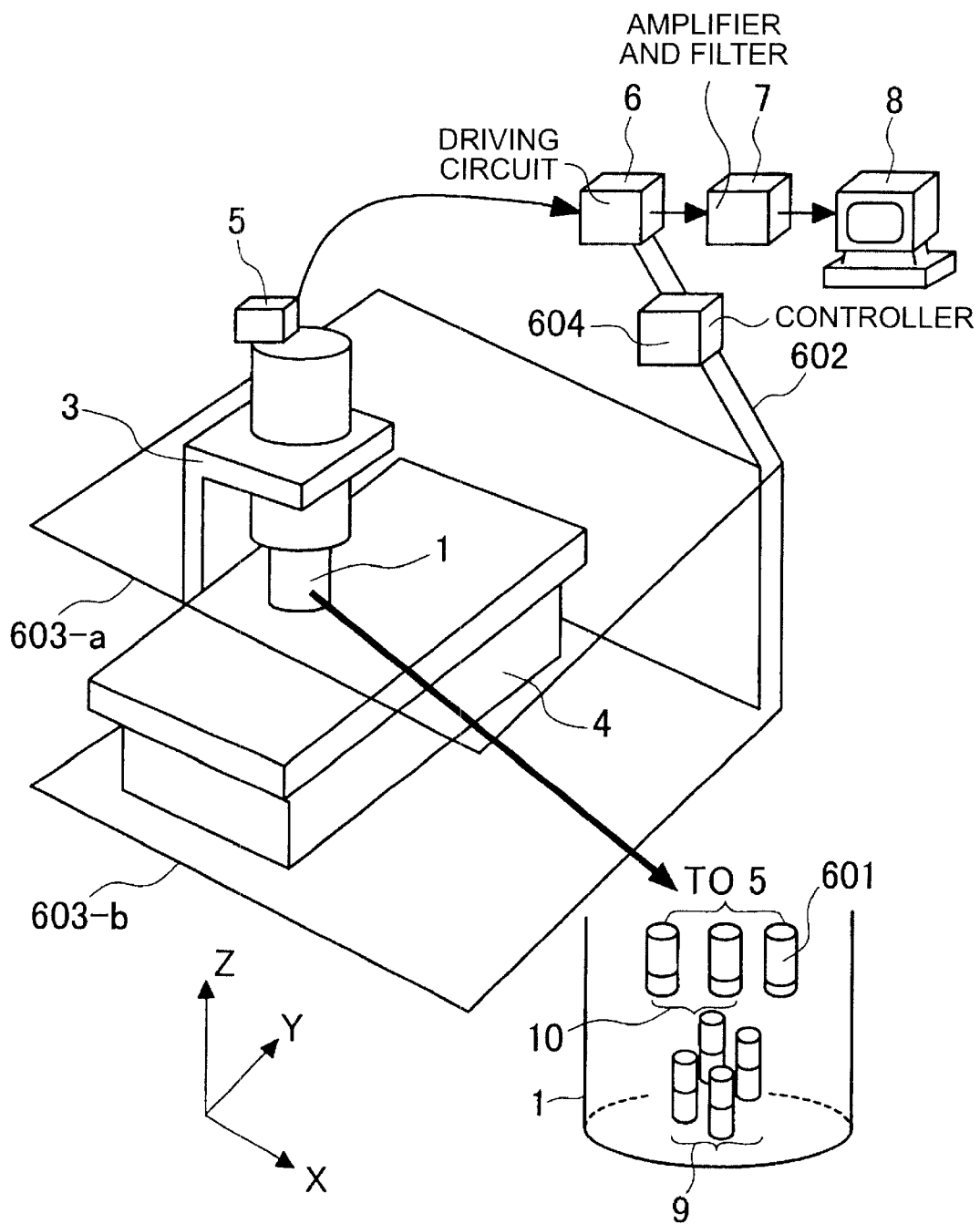
FIG. 23 is a schematic illustration showing an example of the configuration of a magnetic field measuring apparatus according to a preferred Embodiment 3 of the present invention.

FIG. 23 is a schematic illustration showing an example of the configuration of a magnetic field measuring apparatus according to a preferred Embodiment 3 of the present invention. Embodiment 3 is configured without using the magnetically shielded room made of high-permeability material such as permalloy used in Embodiment 1 (FIG. 1) and Embodiment 2 (FIG. 8). The gradiometers for compensation 10 shown in FIG. 23 have the same construction as the gradiometers for compensation 10 (10-*a* and 10-*b*) included in Embodiment 1 (FIG. 1) and Embodiment 2 (FIG. 8).

The baselines of the gradiometers for compensation 10 (10-*a* and 10-*b*) are shorter than the baselines of the gradiometers for detection 9 also in this configuration, but another gradiometer for compensation 601 is placed by the side of the gradiometers for compensation 10 in Embodiment 3. The output from the gradiometer for compensation 601 is used for a controller 604 to control the current flowing through the coils 603-*a* and 603-*b* such that a magnetic field which exerts force in a direction opposite to external magnetic noise is generated in the z direction to cancel the external magnetic noise by 20 dB to 60 dB. The coils 603-*a* and 603-*b* may be placed inside or outside a magnetically shielded room made of aluminum, copper, or the like, the room blocking out high-frequency electromagnetic waves.

The baseline of the gradiometer for compensation 601 shall be shorter than the baselines of the gradiometers for compensation 10 (10-*a* and 1-*b*). Set the baseline of the gradiometer for compensation 601 at, for example, a length falling within a range of 0.5 mm to 1 mm such that external magnetic noise mainly determined only by noise cancellation rates will be canceled.

If the baselines of the gradiometers for detection 10 and 601 are set too short, the coil inductance becomes smaller and the effective coil area is reduced, and consequently, the value of resolution of minimal magnetic fields (e.g., 10 fT/$\sqrt{Hz}$) of the SQUID gradiometers becomes larger. In the configuration shown in FIG. 23, therefore, the areas of the gradiometers for compensation 10 (10-1 and 10-*b*) and the gradiometer for compensation 601 shall be larger than the areas of the gradiometers for detection 9.

Unless the gradiometers for compensation with a smaller value of resolution of minimal magnetic fields than the corresponding value of the gradiometers for detection are used, a problem arises that white noise of the SQUID gradiometers increases when the procedures for canceling external magnetic noise, as explained with FIGS. 4 and 5, are executed or when external magnetic noise is canceled by the coils 603-*a* and 603-B shown in FIG. 23.

If this white noise value is so large as to cause a problem, the increase of white noise accompanied by the processing of external magnetic noise cancellation can be prevented by limiting the signal wave band to a certain bandwidth for the output waveforms from the gradiometers for compensation 10-*a*, 10-*b*, and 601 through analog or digital filtering. Because a magnetic field of a low frequency (up to 1 Hz) is a main source of external magnetic noise in many cases, this band limitation measure is a practical and effective method.

The application of the band limitation measure and the requirement that the areas of gradiometers for compensation are larger than the areas of gradiometers for detection 9, explained above, are not limited to Embodiment 3 (FIG. 23) and Embodiment 4 (FIG. 24) which will be explained below. These measure and requirement may also apply to Embodiment 1 (FIGS. 1 and 2) such that external magnetic noise cancellation can be executed without increasing white noise.

Embodiment 4

Figure 24:
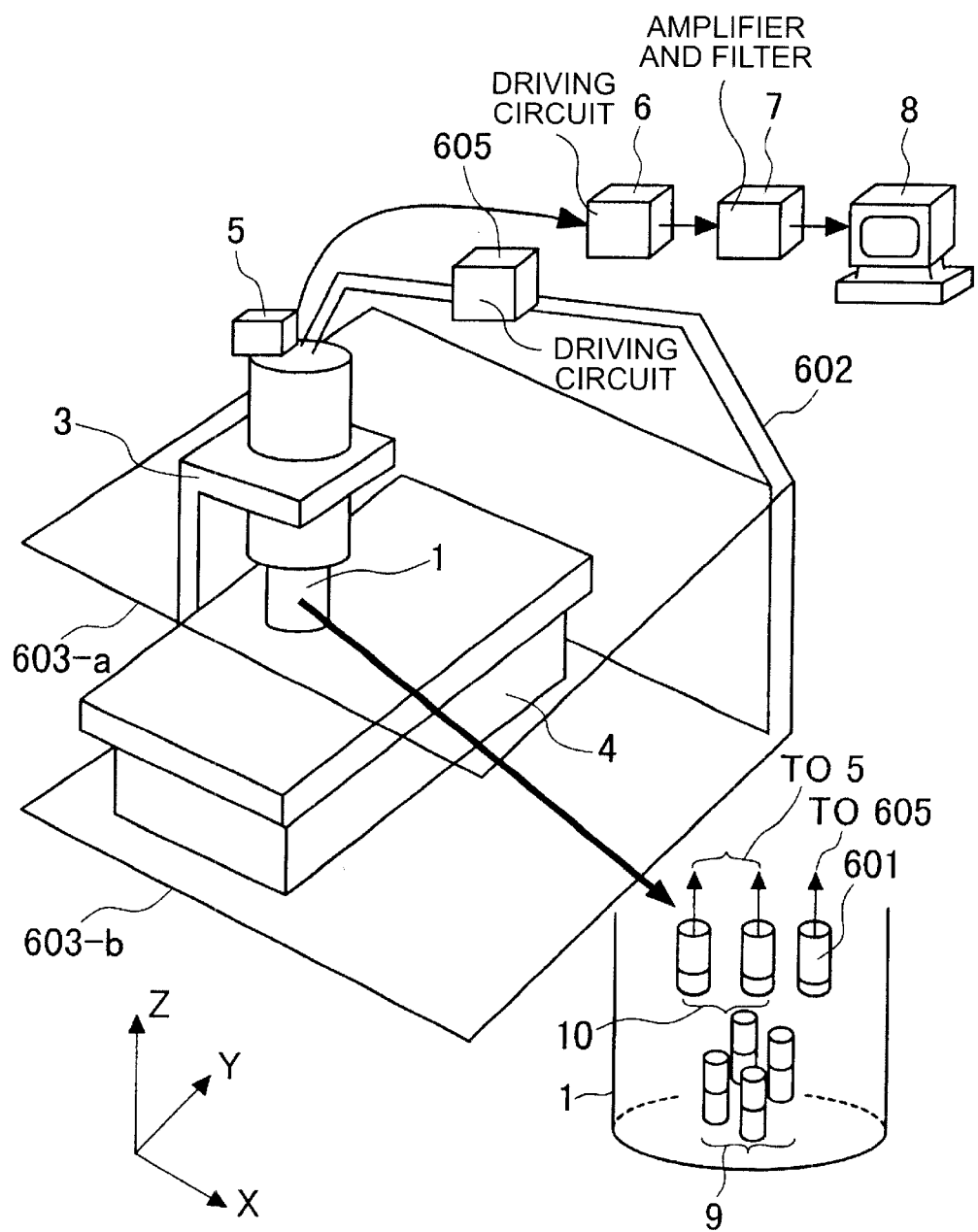
FIG. 24 is a schematic illustration showing an example of the configuration of a magnetic field measuring apparatus according to a preferred Embodiment 4 of the present invention.

FIG. 24 is a schematic illustration showing an example of the configuration of a magnetic field measuring apparatus according to a preferred Embodiment 4 of the present invention. Of this configuration, the difference from the configuration of Embodiment 3 (FIG. 23) will be explained below. The configuration of Embodiment 4 includes a separate driving circuit (FLL: Flux Locked LOOP) 605 to drive the gradiometer for compensation explained in Embodiment 3 (FIG. 23). The coils 603-*a* and 603-*b* also serve as the feedback coils (usually, installed inside of the SQUID) used in the FLL circuit. Because the coils 603-*a* and 603-*b* double noise-canceling coils and feedback coils, external magnetic noise cancellation can be executed without adjustment.

Embodiment 5

Figure 25:
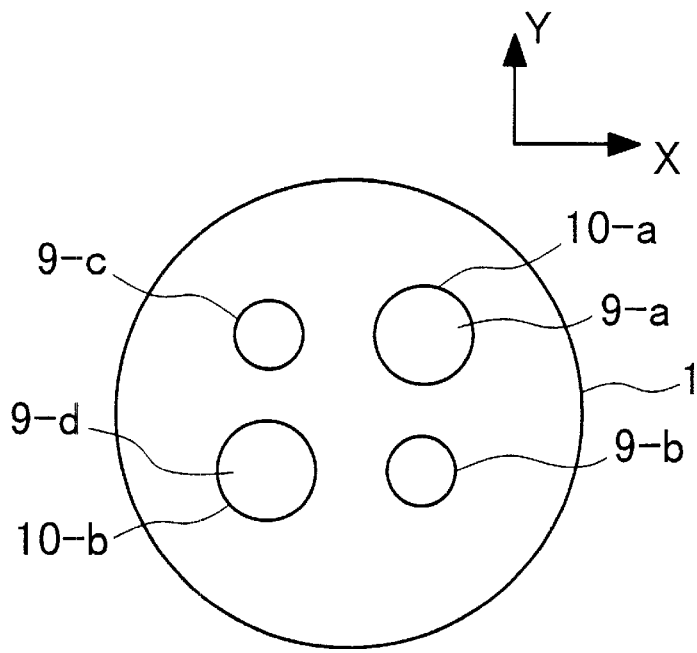
FIG. 25 is an illustration of a preferred Embodiment 5 of the present invention, a projection showing an example of the arrangement of the gradiometers for compensation and the gradiometers for detection in Embodiment 1 (FIGS. 1 and 2) and Embodiment 2 (FIG. 8)

FIG. 25 is an illustration of a preferred Embodiment 5 of the present invention, a projection showing an example of the arrangement of the gradiometers for compensation and the gradiometers for detection in Embodiment 1 (FIGS. 1 and 2) and Embodiment 2 (FIG. 8). This is a top view of the gradiometers by projecting from above the upper arrangement of the gradiometers for compensation on the plane (parallel with the bottom surface of the cryostat) on which the gradiometers for detection are arranged. In the example shown in FIG. 25, the gradiometer for compensation 10-*a* is positioned over the gradiometer for detection 9-*a* and the gradiometer for compensation 10-*b* is positioned over the gradiometer for detection 9-*d*. In the positions of the gradiometers for detection 9-*a* and 9-*d*, observed signals are of relatively small amplitude of the magnetic field originating from the object to be inspected, such as a heart of the human body. Thus, the gradiometers for compensation 10-*a* and 10-*b* can detect substantially pure external magnetic noise almost without receiving the signal inputs of the magnetic field originating from the object such as a heart in the example of arrangement shown in FIG. 25.

Embodiment 6

Figure 26:
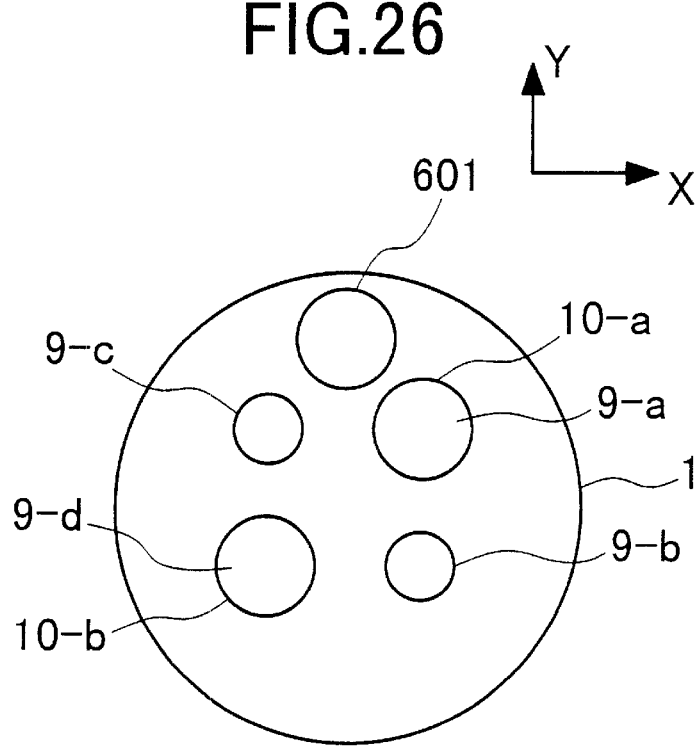
FIG. 26 is an illustration of a preferred Embodiment 6 of the present invention, a projection showing an example of the arrangement of the gradiometers for compensation and the gradiometers for detection in Embodiment 3 (FIG. 23) and Embodiment 4 (FIG. 24).

FIG. 26 is an illustration of a preferred Embodiment 6 of the present invention, a projection showing an example of the arrangement of the gradiometers for compensation and the gradiometers for detection in Embodiment 3 (FIG. 23) and Embodiment 4 (FIG. 24). This is a top view of the gradiometers by projecting from above the upper arrangement of the gradiometers for compensation on the plane (parallel with the bottom surface of the cryostat) on which the gradiometers for detection are arranged. In the example shown in FIG. 26, in addition to the arrangement shown in FIG. 25, the gradiometer for compensation 601 is placed near the gradiometer for compensation 10-*a*. In this example of arrangement shown in FIG. 26, the gradiometer for compensation 601 can also detect substantially pure external magnetic noise almost without receiving the signal inputs of the magnetic field originating from the object such as a heart.

Embodiment 7

In the above description of Embodiments 1 to 6, a 4-channel magnetic field measuring apparatus with four gradiometers for detection was explained. However, the number of gradiometers for detection is not limited to four, of course; i.e., any number of gradiometers may be used, selectable from among, for example, n=1, 2, . . . 15, providing the magnetic field measuring apparatus with $n^2$ channels. Moreover, a plurality of units of each of the gradiometers for compensation, 10-*a*, 10-*b*, and 601 may be used. Specifically, a plurality of gradiometers for compensation having same baseline length may be used and the magnetic signal waveforms measured by these gradiometers averaged. By using the average waveform, external magnetic noise cancellation may be executed, according to the procedures explained for the above Embodiments.

Embodiment 8

In the above description of Embodiments 1 to 7, the apparatus's magnetic field detecting section consisting of the gradiometers for detection and the gradiometers for compensation, both for detecting normal-component signals in a normal direction (z direction) of a magnetic field, was explained as an example. However, the external magnetic noise cancellation methods of the present invention, of course, may apply to a case where the apparatus's magnetic field detecting section consists of the gradiometers for detection and the gradiometers for compensation, both for detecting signals of three-directional (x, y, and z directions) components of a magnetic field, in the same manner as in the above Embodiments 1 to 7.

Specifically, first SQUID gradiometers detect signals of x, y, and z directional components of a biomagnetic field originating from a living body and second SQUID gradiometers detect signals of x, y, and z directional components of external magnetic noise. By using the signals detected by the second gradiometers, each directional component of external magnetic noise is eliminated (canceled) from each corresponding directional component of the signals detected by the first gradiometers, and thus each directional component of the biomagnetic field can be separated and extracted.

Furthermore, distorted magnetic signal waveforms in x, y, and z directional components of a magnetic field, occurring due to the frequency property of the magnetically shielded room in which the apparatus is installed, can be eliminated by using theoretical equations.

Embodiment 9

As shown in FIG. 21 explained in the description of Embodiment 2, on the waveform display on the screen of a display device, a straight-line indicator of the time reading corresponding to the initial point at which external magnetic noise begins to occur is displayed. During the operation of a magnetic field measuring apparatus that can be configured in Embodiments 1 to 8 explained above, moreover, the associated display device may display: magnetic signal waveforms (e.g., those shown in FIG. 9) measured by the flux-gate magnetometer; magnetic signal waveforms (e.g., those shown in FIG. 10) measured by the flux-gate magnetometer and the SQUID gradiometers; magnetic signal waveforms (e.g., those shown in FIGS. 11 and 15) measured by the SQUID gradiometers; magnetic signal waveforms during the progress of executing external magnetic noise cancellation (e.g., those shown in FIGS. 12, 13, 16, and 17); magnetic signal waveforms as the result of external magnetic noise cancellation (e.g., those shown in FIGS. 14, 18, and 21); and other waveforms. By equipping the apparatus with such display, the condition of external magnetic noise occurring as well as the condition of magnetic signal waveforms as the result of external magnetic noise cancellation can be analyzed and evaluated. Further detailed evaluation can also be performed as to whether signal processing gives magnetic signal waveforms fine enough to be used for diagnosis.

Embodiment 10

In the above description of Embodiments 1 to 9, it is assumed that the coils of first-order gradiometers are used as differential-type pickup coils. However, the coils of second-order gradiometers may be used as differential-type pickup coils to configure the apparatus of any of the Embodiments 1 to 8, and the apparatus also can execute external magnetic noise cancellation in the same manner as described for Embodiments 1 to 9.

If the employed differential type pickup coils are the coils of second-order gradiometers, the input coil of any gradiometer for detection and for compensation is the first coil of the coils to constitute the second-order gradiometer, positioned the nearest to the object to be inspected.

The compensating coils of any gradiometer for detection and for compensation are second, third, and fourth coils whose base surface is parallel with the base surface of the first coil of the coils to constitute the second-order gradiometer, serially positioned in order farther than the first coil away from the object to be inspected. The compensating coils shall be made such that the second coil area equals the third coil area in this embodiment.

The baselines of any gradiometer for detection and for compensation are the baselines formed by the coils of the second-order gradiometer; i.e., a distance between the base surfaces of the first and second coils and a distance between the base surfaces of the third and fourth coils. The baselines, or the above distances shall be equal in this embodiment.

When it is assumed that the area of the first coil (input coil) is $s_1$, the respective area of the second and third coils (compensating coils) is $s_2$, the area of the fourth coil (compensating coil) is $s_3$, and the baseline is b, magnetic flux $\phi$ detected by a gradiometer comprising the coils of second-order gradiometer is calculated in the same way as for a gradiometer comprising the coils of first-order gradiometer, as will be expressed by equation 42. The base surface of the first coil is assumed to be positioned at $z=z_1$; the base surface of the second coil at $z=z_2=z_1+b$; the base surface of the third coil at $z=z_2+\Delta=z_1+b+\Delta$, where $\Delta\approx 0$; and the base surface of the fourth coil at $z=z_2+b=z_2+2b$.

$$\phi=s_1\times B(z_1)-2s_2\times B(z_1+b)+s_3\times B(z_1+2_b)=s_1\times\{\beta\times z_1+B(z_0)\}-2s_2\times\{\beta\times(z_1+b)+B(z_0)\}+$$

$$s_3\times\{\beta\times(z_1+b)+B(z_0)\}=\beta\times\{(s_1-s_2)-(s_2+s_3)\}\times z_1+\{(s_1-s_2)-(s_2-s_3)\}\times B(z_0)-2(s_2-s_3)\times\beta\times b \quad \text{[Equation 42]}$$

In equation 42, substituting $S_1$ for $(s_1-s_2)$, $S_2$ for $(s_2-s_3)$, and d for $2\times b$ makes equation 42 equivalent to equation 3. Using equation 43 that defines $\alpha'$, equation 44 gives the solution of $B'_0=\phi/(s_1-s_2)$.

$$\alpha'=(s_2-s_3)/(s_1-s_2) \quad \text{[Equation 43]}$$

$$B'_0=\phi/(s_1-s_2)=\beta\times(1-\alpha')\times z_1+(1-\alpha')\times B(z_0)-2\alpha'\times\beta\times b \quad \text{[Equation 44]}$$

In equation 44, substituting $\alpha$ for $\alpha'$ and d for $2\times b$ makes equation 44 equivalent to equation 5.

In equation 44, a value of $(1-\alpha')$ represents a noise cancellation rate for an uniform magnetic field of the coils of a second-order gradiometer. If equation 2 gives magnetic field distribution in the space in which the gradiometers for detection and the gradiometers for compensation are arranged, the calculation of a magnetic field to be detected includes terms dependent on a coefficient of noise cancellation rate $(1-\alpha')$ and a term dependent on a coefficient of baseline d, as apparent from equation 44.

In order to prevent the signals of a magnetic field originating from the object such as a heart to be inspected from mixing with the signals measured by the gradiometers for compensation, the baselines of the gradiometers for compensation are set shorter than the baselines of the gradiometers for detection as in Embodiment 1. A plurality of gradiometers for compensation having different baseline lengths, for example, 10 mm and 30 mm, are in place. As in Embodiment 1, thus, external magnetic noise cancellation can be executed, according to the first method of canceling external magnetic noise by following the procedures shown in FIGS. 4 and 5. The detected magnetic field originating from the object can be compensated for different quantity of external magnetic noise mixed into it due to that the baselines of the gradiometers for detection and the baselines of the gradiometers for compensation differ in length.

As in Embodiment 1, by using the magnetic signal waveform $B_r(t)$ described by equation 30, magnetic signal waveform $B'_1(t)$ that is measured by the gradiometers for detection comprising the coils of second-order gradiometers can be calculated by equation 45. Here, the time constant of the first coil (input coil) of the second-order gradiometers for detection is $t_1$, the time constant of the second and third coils (compensating coils) is $t_2$, and the time constant of the fourth coil (compensating coil) is $t_3$. Taylor expansion of equation 45 yields equation 46.

$$B'_1(t)=\exp(-t/t_1)-2\times\exp(-t/t_2)+\exp(-t/t_3)=-\{1-\exp(-t(1/t_1-1/t_2))\}\times \exp(-t/t_2)-\{1-\exp(-t(1/t_3-1/t_2))\}\times\exp(-t/t_2) \quad \text{[Equation 45]}$$

$$B'_1(t)=\{(1/t_2-1/t_1)-(1/t_3-1/t_2)\}\times t\times\exp(-t/t_2) \quad \text{[Equation 46]}$$

Similarly, for the gradiometers for compensation comprising the coils of second-order gradiometers, when time constant $t'_1$ for the first coil (input coil), time constant $t'_2$ for the second and third coils (compensating coils), and time constant $t'_3$ for the fourth coil (compensating) are assigned, magnetic signal waveform $B'_2(t)$ that is measured by the gradiometers for Compensation can be calculated by equation 47.

$$B'_2(t)=\{(1/t'_2-1/t'_1)-(1/t'_3-1/t'_2)\}\times t\times\exp(-t/t'_2) \quad \text{[Equation 47]}$$

By using $\delta'$ defined by equation 48, the magnetic signal waveform $B'_2(t)$ of the external magnetic noise measured by the gradiometers for compensation is canceled from the magnetic signal waveform $B'_1(t)$ measured by the gradiometers for detection. Then, magnetic signal waveform $(B'_1-\delta'B'_2)$ is obtained as will be described by equation 49. Taylor expansion of equation 49 yields equation 50.

$$\delta'=\{(1/t_2-1/t_1)-(1/t_3-1/t_2)\}/\{(1/t'_2-1/t'_1)-(1/t'_3-1/t'_2)\} \quad \text{[Equation 48]}$$

In equation 48, substituting $(1/T_2)$ for $(1/t_2-1/t_1)$, $(1/T_1)$ for $(1/t_3-1/t_2)$, $(1/T_4)$ for $(1/t'_2-1/t'_1)$, and $(1/T_3)$ for $(1/t'_3-1/t'_2)$ makes equation 48 equivalent to equation 34.

$$(B'_1-\delta'B'_2)=\{(1/t'_2-1/t'_1)-(1/t'_3-1/t'_2)\}\times\delta'\times t\times\exp(-t/t_2)-$$

$$\delta'\times\{(1/t'_2-1/t'_1)-(1/t'_3-1/t'_2)\}\times t\times\exp(-t/t'_2)=$$

$$\{(1/t'_2-1/t'_1)-(1/t'_3-1/t'_2)\}\times\delta'\times t\times\{\exp(-(1/t_2-1/t'_2)\times t)-1\}\times\exp(-t/t'_2) \quad \text{[Equation 49]}$$

$$(B'_1-\delta'B'_2)=-(1/t_2-1/t'_2)\times\{(1/t'_2-1/t'_1)(1/t'_3-1/t'_2)\}\times\delta'\times t^2\times\exp(-t/t'_2) \quad \text{[Equation 50]}$$

If the time-independent terms of the amplitude expressions in equation 50 are substituted by $\eta'$ (equation 51), equation 50 becomes a function as will be expressed by equation 52. As described above, equation 52 expresses the magnetic signal waveform obtained by canceling the external magnetic noise $B'_2(t)$ from the detected waveform $B'_1(t)$, using a fitting parameter $\delta'$ determined by equation 48.

$$\eta'=-(1/t_2-1/t'_2)\times\{(1/t'_2-1/t'_1)-(1/t'_3-1/t'_2)\}\times\delta'- \quad \text{[Equation 51]}$$

$$(B'_1-\delta'B'_2)=\eta'\times t^2\times\exp(-t/t'_2) \quad \text{[Equation 52]}$$

In equation 52, substituting η for η' and $T_3$ for $t'_2$ makes equation 52 equivalent to equation 38.

Because equation 52 is equivalent to equation 38, the second method of canceling external magnetic noise shown in FIG. 7 (the method of canceling the external magnetic noise due to the frequency property of the magnetically shielded room) can be applied to cases where the coils of second-order gradiometers are used as differential-type pickup coils in the same manner as in embodiment 1.

As explained above, external magnetic noise cancellation can be executed by alternatively using the coils of second-order gradiometers as differential-type pickup coils in Embodiments 1 to 9 in exactly the same manner as for cases where the coils of first-order gradiometers are used as differential-type pickup coils. If second-order gradiometers are used to configure the invention, external magnetic noise from sources in more extensive area can be canceled.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A magnetic field measuring apparatus which enables external magnetic noise cancellation, comprising:
   a plurality of first SQUID gradiometers to detect signals in a normal direction of a magnetic field originating from an object to be inspected;
   a second SQUID gradiometer to detect signals in a normal direction of external magnetic noise, wherein said second SQUID gradiometer is separated from said first SQUID gradiometers and is located in a position above said first SQUID gradiometers;
   a cryogenic enclosure to keep said first and second SQUID gradiometers cold;
   a driving circuit to drive said first and second SQUID gradiometers;
   a computer to execute signal processing for canceling the external magnetic noise included in magnetic signals detected by said first SQUID gradiometers, using the external magnetic noise signals detected by said second SQUID gradiometer, after collecting the signals detected by said first and second squid gradiometers; and
   a display means to display the results of signal processing, wherein
   said first and second SQUID gradiometers comprise differential-type pickup coils and
   a baseline length of said differential-type pickup coils of said second SQUID gradiometer is shorter than a baseline length of said differential-type pickup coils of said first SQUID gradiometers.

2. The magnetic field measuring apparatus according to claim 1, wherein said apparatus placed in a magnetically shielded room detects said signals in a normal direction of a magnetic field originating from said object to be inspected and includes a single unit or a plurality of units of second SQUID gradiometers,
   said computer executes
   first signal processing by using the external magnetic noise signals detected by said second SQUID gradiometer, mixed magnetic signals which are formed by mixing said external magnetic noise signals, and the magnetic signals detected by said first SQUID gradiometers and, by applying a method of least squares, thus canceling said external magnetic noise from said mixed magnetic signals, and
   second signal processing in such a manner that said computer executes approximation of waveform B(t) which represents external magnetic noise occurring due to the frequency property of said magnetically shielded room with its magnetic field strength changing as a function of time near the initial time at which said external magnetic noise begins to occur due to said frequency property of said magnetically shielded room by using equation $B(t)=-A\cdot t^2\cdot\exp(-t/T)$, where A is amplitude, T is time constant, and t is time variable, calculates said amplitude A and said time constant T, according to the method of least squares, by using the magnetic signal waveform obtained through said first processing, and cancels said external magnetic noise occurring due to said frequency property of said magnetically shielded room from the magnetic signal waveform obtained through said first signal processing by using said waveform B(t) determined by the method of least squares.

3. The magnetic field measuring apparatus according to claim 2, wherein said computer infers said initial time and said inferred initial time is indicated on the time axis for showing a magnetic signal waveform from which said external magnetic noise has been canceled by said first and second signal processing.

4. The magnetic field measuring apparatus according to claim 1, wherein a pickup coil area of said differential-type pickup coils of said second SQUID gradiometer(s) is greater than a pickup coil area of said differential-type pickup coils of said first SQUID gradiometers.

5. A magnetic field measuring apparatus which enables external magnetic noise cancellation, comprising:
   a plurality of first SQUID gradiometers to detect signals in a normal direction of a magnetic field originating from an object to be inspected within a magnetically shielded room;
   a second SQUID gradiometer to detect signals in a normal direction of external magnetic noise, wherein said second SQUID gradiometer is separated from said first SQUID gradiometers and is located in a position above said first SQUID gradiometers;
   a cryogenic enclosure to keep said first and second SQUID gradiometers cold;
   a driving circuit to drive said first and second SQUID gradiometers;
   a computer to execute signal processing after collecting the signals detected by said first and second SQUID gradiometers; and
   a display means to display the results of signal processing, wherein
   said first and second SQUID gradiometers comprise differential-type pickup coils,
   a baseline length of said differential-type pickup coils of said second SQUID radiometer is shorter than a baseline length of said differential-type pickup coils of said first SQUID gradiometers, and said computer executes, by using the external magnetic noise signals detected by said second SQUID gradiometers and magnetic signals detected by said first SQUID gradiometers, signal processing (a) to cancel said external magnetic noise due to variant noise cancellation rates of said first SQUID gradiometers from the magnetic signal waveform obtained through detection by said first SQUID gradiometers and signal processing (b) to cancel said external magnetic noise occurring due to the frequency property of said magnetically shielded room from the magnetic signal waveform obtained through said signal processing (a).

6. The magnetic field measuring apparatus according to claim 5, wherein said computer infers initial time at which said external magnetic noise begins to occur due to said frequency property of said magnetically shielded room and said inferred initial time is indicated on the time axis for showing a magnetic signal waveform from which said external magnetic noise has been canceled by said signal processing (a) and (b).

7. The magnetic field measuring apparatus according to claim 5, wherein a pickup coil area of said differential-type pickup coils of said second SQUID gradiometer is greater than a pickup coil area of said differential-type pickup coils of said first SQUID gradiometers.

8. A magnetic filed measuring apparatus which enables external magnetic noise cancellation, comprising:

a plurality of first SQUID gradiometers to detect signals in a normal direction of a magnetic field originating from an object to be inspected within a magnetically shielded room;

second and third SQUID gradiometers to detect signals in a normal direction of external magnetic noise, wherein said second and third SQUID gradiometers are separated from said first SQUID gradiometers and are located in a position above said first SQUID gradiometers;

a cryogenic enclosure to keep said first, second, and third SQUID gradiometers cold;

a driving circuit to drive said first, second, and third SQUID gradiometers;

a computer to execute signal processing after collecting the signals detected by said first, second, and third SQUID gradiometers; and a display means for displaying the results of signal processing, wherein said first, second, and third SQUID gradiometers comprise differential-type pickup coils, a baseline lengths of said differential-type pickup coils of said second and third SQUID gradiometers are shorter than a baseline length of said differential-type pickup coils of said first SQUID gradiometers, the baseline length of said differential-type pickup coils of said second SQUID gradiometer is shorter than the baseline length of said differential-type pickup coils of said third SQUID gradiometer, and said computer executes, by using the external magnetic noise signals detected by said second and third SQUID gradiometers and magnetic signals detected by said first SQUID gradiometers, signal processing (a) to cancel said external magnetic noise due to variant noise cancellation rates of said first SQUID gradiometers from the magnetic signal waveform obtained through detection by said first SQUID gradiometers, signal processing (b) to cancel said external magnetic noise due to that said baseline of said differential-type pickup coils of said second SQUID gradiometer differs from said baseline of said differential-type pickup coils of said third SQUID gradiometer from the magnetic signal waveform obtained through said signal processing (a), and signal processing (c) to cancel said external magnetic noise occurring due to the frequency property of said magnetically shielded room from the magnetic signal waveform obtained through said signal processing (b).

9. The magnetic field measuring apparatus according to claim 8, wherein said computer infers initial time at which said external magnetic noise begins to occur due to said frequency property of said magnetically shielded room and said inferred initial time is indicated on the time axis for showing a magnetic signal waveform from which said external magnetic noise has been canceled by said signal processing (a), (b), and (c).

10. The magnetic field measuring apparatus according to claim 8, wherein a pickup coil area of said differential-type pickup coils of said second and third SQUID gradiometers is greater than a pickup coil area of said differential-type pickup coils of said first SQUID gradiometers.

11. A magnetic field measuring apparatus which enables external magnetic noise cancellation, comprising:

a plurality of first SQUID gradiometers to detect signals in a normal direction of a magnetic field originating from an object to be inspected within a magnetically shielded room which blocks out high-frequency electromagnetic waves;

a plurality of second SQUID gradiometers to detect signals in a normal direction of external magnetic noise, wherein said second SQUID gradiometers are separated from said first SQUID gradiometers and are located in a position above said first SQUID gradiometers;

a cryogenic enclosure to keep said first and second SQUID gradiometers cold;

a driving circuit to drive said first and second SQUID gradiometers;

noise-canceling coils positioned over and under said object to be inspected to generate a magnetic field that cancels said external magnetic noise;

a control means to control the current flowing through said noise-canceling coils; and a computer to execute signal processing for canceling the external magnetic noise included in magnetic signals detected by said first SQUID gradiometers, using the external magnetic noise signals detected by said second SQUID gradiometer, after collecting the signals detected by said first and second SQUID gradiometers, wherein said first and second Squid gradiometers comprise differential-type pickup coils, a baseline length of said differential-type pickup coils of said second SQUID gradiometers is shorter than a baseline length of said differential-type pickup coils of said first SQUID gradiometers, said control means controls the current flowing through said noise-canceling coils on the basis of the output from one SQUID gradiometer of said second SQUID gradiometers, and said noise-canceling coils generate a magnetic field that exerts force in a direction opposite to said external magnetic noise.

12. The magnetic field measuring apparatus according to claim 11, wherein a pickup coil area of said differential-type pickup coils of said second SQUID gradiometers is greater than a pickup coil area of said differential-type pickup coils of said first SQUID gradiometers.

13. The magnetic field measuring apparatus according to claim 11, wherein a separate driving circuit is provided to drive said one SQUID gradiometer of said second SQUID gradiometers and said noise-canceling coils also serve as feedback coils to be used in said separate driving circuit.

14. The magnetic field measuring apparatus according to claim 11, wherein said noise-canceling coils are placed inside or outside said magnetically shielded room.

15. The magnetic field measuring apparatus according to claim 1, wherein said object to be inspected is a living body.

16. The magnetic field measuring apparatus according to claim 5, wherein said object to be inspected is a living body.

17. The magnetic field measuring apparatus according to claim 8, wherein said object to be inspected is a living body.

18. The magnetic field measuring apparatus according to claim 11, wherein said object to be inspected is a living body.

* * * * *